(12) United States Patent
Duggal et al.

(10) Patent No.: US 11,186,529 B2
(45) Date of Patent: Nov. 30, 2021

(54) ADVANCED OXIDATIVE COUPLING OF METHANE

(71) Applicant: Lummus Technology LLC, The Woodlands, TX (US)

(72) Inventors: Suchia Duggal, San Rafael, CA (US); Guido Radaelli, South San Francisco, CA (US); Jarod McCormick, San Carlos, CA (US); Andrew Aronson, San Bruno, CA (US); Joel Cizeron, Redwood City, CA (US)

(73) Assignee: LUMMUS TECHNOLOGY LLC, The Woodlands, TX (US)

( * ) Notice: Subject to any disclaimer, the term of this patent is extended or adjusted under 35 U.S.C. 154(b) by 145 days.

(21) Appl. No.: 16/445,562

(22) Filed: Jun. 19, 2019

(65) Prior Publication Data

US 2020/0172452 A1    Jun. 4, 2020

Related U.S. Application Data

(63) Continuation of application No. 14/868,911, filed on May 29, 2015, now abandoned.
(Continued)

(51) Int. Cl.
*C07C 2/82*     (2006.01)
*C07C 7/152*    (2006.01)
(Continued)

(52) U.S. Cl.
CPC ............... *C07C 2/82* (2013.01); *C07C 1/04* (2013.01); *C07C 1/12* (2013.01); *C07C 2/06* (2013.01);
(Continued)

(58) Field of Classification Search
CPC .. C07C 2/82; C07C 7/152; C07C 1/04; C07C 1/12; C07C 2/06; C07C 2/42; C07C 4/02;
(Continued)

(56) References Cited

U.S. PATENT DOCUMENTS 2,324,172 A    7/1943 Parkhurst
2,486,980 A    11/1949 Robinson
(Continued)

FOREIGN PATENT DOCUMENTS

CA    2041874 C    4/1999
CA    2765769 A1   1/2011
(Continued)

OTHER PUBLICATIONS

Extended European Search Report for EP Application No. 20203394.0 dated Jan. 25, 2021.
(Continued)

*Primary Examiner* — Thuan D Dang
(74) *Attorney, Agent, or Firm* — Calfee, Halter & Griswold LLP

(57) ABSTRACT

The present disclosure provides a method for generating higher hydrocarbon(s) from a stream comprising compounds with two or more carbon atoms ($C_{2+}$), comprising introducing methane and an oxidant (e.g., $O_2$) into an oxidative coupling of methane (OCM) reactor that has been retrofitted into a system comprising an ethylene-to-liquids (ETL) reactor. The OCM reactor reacts the methane with the oxidant to generate a first product stream comprising the $C_{2+}$ compounds. The first product stream can then be directed to a pressure swing adsorption (PSA) unit that recovers at least a portion of the $C_{2+}$ compounds from the first product stream to yield a second product stream comprising the at least the portion of the $C_{2+}$ compounds. The second product stream can then be directed to the ETL reactor. The higher hydro-
(Continued)

carbon(s) can then be generated from the at least the portion of the $C_{2+}$ compounds in the ETL reactor.

8 Claims, 22 Drawing Sheets

Related U.S. Application Data

(60) Provisional application No. 62/141,789, filed on Apr. 1, 2015.

(51) Int. Cl.

| | |
|---|---|
| F01K 5/00 | (2006.01) |
| C07C 1/04 | (2006.01) |
| C07C 1/12 | (2006.01) |
| C07C 2/06 | (2006.01) |
| C07C 2/42 | (2006.01) |
| C07C 4/02 | (2006.01) |
| C25B 1/04 | (2021.01) |
| F01K 23/06 | (2006.01) |
| F01K 25/10 | (2006.01) |
| H01L 35/30 | (2006.01) |

(52) U.S. Cl.
CPC ............ *C07C 2/42* (2013.01); *C07C 4/02* (2013.01); *C07C 7/152* (2013.01); *C25B 1/04* (2013.01); *F01K 5/00* (2013.01); *F01K 23/067* (2013.01); *F01K 25/103* (2013.01); *H01L 35/30* (2013.01); *Y02E 60/36* (2013.01); *Y02P 20/129* (2015.11)

(58) Field of Classification Search
CPC ........ F01K 5/00; F01K 23/067; F01K 25/103; C25B 1/04; H01L 35/30; Y02E 60/36; Y02E 20/18; Y02P 20/129
See application file for complete search history.

(56) References Cited

U.S. PATENT DOCUMENTS

| | | | |
|---|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,516,262 A | 6/1970 | Bernstein |
| 3,584,071 A | 6/1971 | McNulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A | 9/1978 | Jordan et al. |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A | 11/1983 | Sato et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A | 5/1985 | Huebel |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A | 12/1989 | Campbell et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,113,032 A | 5/1992 | Cameron et al. |
| 5,118,898 A | 6/1992 | Tyler et al. |

(56) References Cited

U.S. PATENT DOCUMENTS

| | | |
|---|---|---|
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Fabio et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 | 8/2003 | Hall et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |

(56) References Cited

U.S. PATENT DOCUMENTS

| | | |
|---|---|---|
| 7,793,517 B2 | 9/2010 | Patel et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0021379 A1 | 2/2006 | Ronczy |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |

(56) References Cited

U.S. PATENT DOCUMENTS

| | | |
|---|---|---|
| 2009/0209412 A1 | 8/2009 | Parent et al. |
| 2009/0209794 A1 | 8/2009 | Laurilzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0022125 A1 | 1/2017 | Fichtl |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |

(56) References Cited

U.S. PATENT DOCUMENTS

| | | | |
|---|---|---|---|
| 2020/0048165 A1 | 2/2020 | Duggal et al. | |
| 2020/0055796 A1 | 2/2020 | Nyce et al. | |
| 2020/0071242 A1 | 3/2020 | Patel et al. | |
| 2020/0189994 A1 | 6/2020 | Radaelli et al. | |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 308447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Duan, et al. Three-dimensional copper (II) metal-organic framework with open metal sites and anthracene nucleus for highly selective C2H2/CH4 and C2NH2/CO2 gas separation at room temperature. Microporous and Mesoporous Materials. vol. 181, Nov. 15, 2013, pp. 99-104.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.
Extended European Search Reported dated Mar. 6, 2019 for European U.S. Appl. No. 16855929.2.
Communication under Rule 71(3) EPC dated Mar. 10, 2020 for European Patent Application No. 16855929.2.
Office Action dated Mar. 13, 2020 for U.S. Appl. No. 16/357,012.
Office Action dated Nov. 30, 2017 for U.S. Appl. No. 15/272,205.
Office Action dated Sep. 25, 2018 for U.S. Appl. No. 15/272,205.
International search report and written opinion dated Feb. 2, 2017 for PCT Application No. PCT/US2016/052959.
Notice of Allowance dated Jan. 8, 2021 for U.S. Appl. No. 16/357,012.
Witek-Krowiak, A et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 03/BaCO3 catalysts. J. Chem. Tech. Biotechnol. 65:351-354, 1996.
Wu, et al., High-Capacity Methane Storage in Metal-Organic Frameworks M2(dhtp): The Important Role of Open Metal Sites, J. Am. Chem. Soc. 131 (13):4995-5000.
Xu, et al. Maximise ethylene gain and acetylene selective hydrogenation efficiency. Petroleum technology quarterly 18.3 (2013): 39-42.
Xu, G et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17: 2304-2310, 2006.

(56) References Cited

OTHER PUBLICATIONS

Yu, et al. Oxidative coupling of methane over acceptor-doped SrTiO3: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal Ions, J Am. Chem. Soc., 2008, 130(46): 15268-69.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
International search report and written opinion dated Aug. 11, 2016 for PCT/US2016/024195.
Office action dated Nov. 6, 2017 for U.S. Appl. No. 14/868,911.
U.S. Appl. No. 14/868,911 Office Action dated May 29, 2018.
Agarwal, et al., Aqueous Au—Pd colloids catalyze selective CH4 oxidation to CH3OH with O2 under mild conditions, Science 358, Oct. 13, 2017, 223-27.
Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.
American Petroleum Institute Publication 534 Heat Recovery Steam Generators Jan. 1995 (51 pages).
Autothermal Partial Oxidative Coupling of Methane. IP.com, Prior Art Database Technical Disclosure, Jul. 29, 2008, 5 pages.
Barrett, et al. The determination of pore volume and area distributions in porous substances—Compuatations from nitrogen isotherms J. Am. Chem. Soc., 1951, vol. 73, pp. 373-380.
Berstad, D. et al. Low-temperature CO2 removal from natural gas. Energy Procedia (2012) 26:41-48.
Bloch, et al. Hydrocarbon Separations in a Metal-Organic Framework with Open Iron(II) Coordination Sites, Science, 2012, 335:1606-1610.
Bollmann, et al. Ethylene tetramerization: a new route to produce 1-octene in exceptionally high selectivities. J Am Chem Soc. Nov. 17, 2004;126(45):14712-3.
Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 03 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Corma, From Microporous to Mesoporous Molecular Sieve Materials and Their Use in Catalysis, Chem. Rev., 97, 1997, pp. 2373-2419.
Debart, et al. α-MN02 Nanowires: A catalyst for the 02 Electrode in Rechargeabl Lithium Batteries. Angewandte Chemie International Edition 47: 4521-4524, 2008.
Dietzl, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li20/Mg0) Catalyst/Porous Alpha-Alumina Composite for the Oxidative Coupling of Methane Reaction, AIChE Journal, Mar. 2010, 56(3):717-28.
Gao, et al. A study on methanol steam reforming to CO2 and H2 over the La2 C04 nanofiber catalyst. Journal of Solid State Chemistry 181: 7-13,2008.
Gao, et al. The direct decomposition of NO over the La2 Cu04 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al., Mesoporous Material from Zeolite, Journal of Poruous Materials, 2002, pp. 43-48.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4 (4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
Hosseinpour, Performance of CaX Zeolite for Separation of C2H6, C2H4, and CH4 by Adsorption Process Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5 (22): 10844-10848, 2013.
Huang, et al. Exploiting shape effects of La2O3 nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.

(56) References Cited

OTHER PUBLICATIONS

Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. Energy and Fuels. 2008, 22:1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 W04—Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 7, pp. 237-242. (Year: 2015).
Morgan, C.R et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Jounral of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 W04/Si02 and MN/NA2 W04/Mg0 Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Simons, K. Membrane Technologies for CO2 Capture. Dissertation, U. of Twente (2010).
Smith, et al. Recent developments in solvent absorption technologies at the CO2CRC in Australia. Energy Procedia 1 (2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 W04/Si02 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 W04/SiO2 Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.

(56) References Cited

OTHER PUBLICATIONS

Wang, et al. Autothermal oxidative coupling of methane on the $SrCO_3/Sm_2O_3$ catalysts. Catalysis communications 10: 807-810, 2009.

Wang, et al. Comparative study on oxidation of methane to ethane and ethylene over $NA_2WO_4$—$Mn/SiO_2$ catalysts prepared by different methods. Journal of Molecular Catalysis A: Chemical 245:272-277, 2006.

Wang, et al. Low temperature selective oxidation of methane to ethane and ethylene over $BaCO_3/La_2O_3$ catalysts prepared by urea combustion method. Catalysis communications 7: 5963, 2006.

Wang, et al., Critical Influence of $BaCO_3$ on Low Temperature Catalytic Activity of $BaCO_3/ZrO_2$ Catalysts for Oxidative Coupling of Methane, Catalysis Letters (2009), 129:156-162.

Water Electrolysis & Renewable Energy Systems. FuelCellToday (May 2013).

Wikipedia search, Adiabatic Process, Mar. 2011, 10 pages.

Chemical Engineering—"Separation Processes: Supercritical $CO_2$: A Green Solvent" Feb. 1, 2010.

ADVANCED OXIDATIVE COUPLING OF METHANE

CROSS-REFERENCE

This application is a Continuation of U.S. application Ser. No. 14/868,911, filed Sep. 29, 2015, which claims priority to U.S. Provisional Patent Application No. 62/141,789, filed Apr. 1, 2015, which are entirely incorporated herein by reference.

BACKGROUND

The modern refining and petrochemical industry makes extensive use of fractionation technology to produce and separate various desirable compounds from crude oil. The conventional fractionation technology is energy intensive and costly to install and operate. Cryogenic distillation has been in use for over a hundred years to separate and recover hydrocarbon products in various refining and petrochemical industries. However, there is a need for non-cryogenic separation methods and systems, particularly for oxidative coupling of methane (OCM) processes.

SUMMARY

Aspects of the present disclosure provide processes for recovering olefins from a stream containing mix of hydrocarbons by utilizing techniques based the use of adsorbents. In some embodiments, systems and methods enable the separation, pre-separation, purification and/or recovery of hydrocarbons, including, but not limited to, olefins, ethylene, propylene, methane, and ethane, and $CO_2$, from a multicomponent hydrocarbon stream such as an effluent stream from an oxidative coupling of methane (OCM) reactor or an ethylene-to-liquids (ETL) reactor. The hydrocarbon stream can also be the feed to the OCM or ETL reactor in certain cases. In certain cases, the feed to the ETL reactor is the effluent from OCM reactor. In some cases, a separation process utilizing adsorbents can be used to purify and pre-treat existing hydrocarbon streams (such as refinery off-gases, cracker off-gas, streams from NGL plants, and others), followed by use of the resulting olefin rich stream (e.g., PSA tail gas) as the ETL feed.

The present disclosure provides various improvements in OCM and ETL processes, such as, without limitation, a separation and pre-separation process to recover desired or predetermined components from an OCM reactor effluent, $CO_2$ recovery and capture techniques, enhanced heat recovery methods to utilize the OCM reaction heat more efficiently, and techniques and technologies to further reduce the carbon footprint of the OCM process.

An aspect of the present disclosure provides a method for generating higher hydrocarbon(s) from a stream comprising compounds with two or more carbon atoms ($C_{2+}$), comprising introducing methane and an oxidant (e.g., $O_2$) into an oxidative coupling of methane (OCM) reactor that has been retrofitted into a system comprising an ethylene-to-liquids (ETL) reactor. The OCM reactor reacts the methane with the oxidant to generate a first product stream comprising the $C_{2+}$ compounds. The first product stream can then be directed to a pressure swing adsorption (PSA) unit that recovers at least a portion of the $C_{2+}$ compounds from the first product stream to yield a second product stream comprising the at least the portion of the $C_{2+}$ compounds. The second product stream can then be directed to the ETL reactor. The higher hydrocarbon(s) can then be generated from the at least the portion of the $C_{2+}$ compounds in the ETL reactor.

In some cases, the first product stream is directed to other intermediate units before the PSA, such as a post-bed cracking (PBC) unit that generates alkenes from alkanes. The alkenes can be included in the first product stream, which can then be directed to the PSA.

In an aspect, the present disclosure provides a method for generating higher hydrocarbon(s) from a stream comprising compounds with two or more carbon atoms ($C_{2+}$), comprising: (a) introducing methane and an oxidant into an oxidative coupling of methane (OCM) reactor that has been retrofitted into a system comprising an ethylene-to-liquids (ETL) reactor, where the OCM reactor reacts the methane with the oxidant to generate a first product stream comprising the $C_{2+}$ compounds; (b) directing the first product stream to a pressure swing adsorption (PSA) unit that recovers at least a portion of the $C_{2+}$ compounds from the first product stream to yield a second product stream comprising the at least the portion of the $C_{2+}$ compounds; (c) directing the second product stream to the ETL reactor; and (d) generating the higher hydrocarbon(s) from the at least the portion of the $C_{2+}$ compounds in the ETL reactor.

In some embodiments, the method further comprises: (e) recovering a light stream comprising (i) hydrogen and (ii) carbon monoxide (CO) and/or carbon dioxide ($CO_2$) from the PSA unit and recycling the light stream to the OCM reactor; (f) directing at least a portion of the light stream into a methanation unit that reacts the hydrogen and the CO and/or $CO_2$ to produce a methanation product stream comprising methane; and (g) directing the methanation product stream into the OCM reactor.

In some embodiments, the method further comprises recovering $C_2$ and/or $C_3$ compounds from the second product stream and directing the $C_2$ and/or $C_3$ compounds to the OCM reactor. In some embodiments, the OCM reactor further comprises a post-bed cracking (PBC) unit.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon monoxide (CO) and/or carbon dioxide ($CO_2$); and (b) directing the product stream from the OCM reactor into a separations system that employs a refrigeration unit having a refrigerant that includes methane from the product stream, to enrich the $C_{2+}$ compounds in the product stream.

In some embodiments, the product stream is directed into the separations system through one or more additional units.

In some embodiments, the method further comprises separating methane from the product stream for use in the refrigeration unit. In some embodiments, the method further comprises directing CO and/or $CO_2$ from the product stream to a methanation reactor that reacts the CO and/or $CO_2$ to yield a methanation product stream comprising methane. In some embodiments, the method further comprises directing at least a portion of the methane in the methanation product stream to the OCM reactor. In some embodiments, the method further comprises separating the product stream into (i) an ethylene product stream comprising ethylene and (ii) a $C_{3+}$ product stream comprising compounds with three or more carbon atoms ($C_{3+}$ compounds). In some embodiments, the method further comprises directing ethane from the product stream to the OCM reactor. In some embodiments, the method further comprises prior to directing the product stream into the separations system, compressing the product stream.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon monoxide (CO) and/or carbon dioxide ($CO_2$); and (b) directing the product stream from the OCM reactor into a separations system that employs a complexation unit having a complexation catalyst that forms pi complexes with the ethylene in the product stream, to enrich the $C_{2+}$ compounds in the product stream.

In some embodiments, the product stream is directed into the separations system through one or more additional units. In some embodiments, the method further comprises using the complexation unit to remove one or more impurities from the product stream, where the impurities are selected from the group consisting of $CO_2$, sulfur compounds, acetylenes, and hydrogen. In some embodiments, the complexation catalyst includes one or more metals selected from the group consisting of silver and copper. In some embodiments, the method further comprises directing CO and/or $CO_2$ from the product stream to a methanation reactor that reacts the CO and/or $CO_2$ to yield a methanation product stream comprising methane. In some embodiments, the method further comprises directing the methane in the methanation product stream to the OCM reactor. In some embodiments, the method further comprises separating the product stream into (i) an ethylene product stream comprising ethylene and (ii) a $C_{3+}$ product stream comprising compounds with three or more carbon atoms ($C_{3+}$ compounds). In some embodiments, the method further comprises directing ethane from the product stream to the OCM reactor. In some embodiments, the method further comprises prior to directing the product stream into the separations system, compressing the product stream.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon dioxide ($CO_2$); and (b) directing the product stream from the OCM reactor into a separations system that employs a $CO_2$ separation unit to separate the $CO_2$ from the product stream, to enrich the $C_{2+}$ compounds in the product stream, which $CO_2$ separation unit employs (i) sorbent or solvent separation of $CO_2$, (ii) membrane separation of $CO_2$, or (iii) cryogenic or low temperature separation of $CO_2$ having an operating temperature greater than a boiling point of methane and less than a boiling point of $CO_2$.

In some embodiments, the product stream is directed into the separations system through one or more additional units. In some embodiments, the sorbent or solvent separation of $CO_2$ employs an amine based absoprtion system. In some embodiments, the sorbent or solvent separation of $CO_2$ employs a Benfield process. In some embodiments, the sorbent or solvent separation of $CO_2$ employs diethanolamine. In some embodiments, the sorbent or solvent separation of $CO_2$ employs glycol dimethylether. In some embodiments, the sorbent or solvent separation of $CO_2$ employs propylene carbonate. In some embodiments, the sorbent or solvent separation of $CO_2$ employs Sulfinol.

In some embodiments, the sorbent or solvent separation of $CO_2$ employs a zeolite. In some embodiments, the sorbent or solvent separation of $CO_2$ employs active carbon. In some embodiments, the $CO_2$ separation system comprises a membrane $CO_2$ separation system. In some embodiments, the membrane separation of $CO_2$ employs a polymeric membrane. In some embodiments, the membrane separation of $CO_2$ employs a metallic membrane. In some embodiments, the membrane separation of $CO_2$ employs a ceramic membrane. In some embodiments, the membrane separation of $CO_2$ employs a hybrid membrane comprising a membrane supporting a solvent or sorbent. In some embodiments, the membrane separation of $CO_2$ employs a poly ionic liquid membrane. In some embodiments, the membrane separation of $CO_2$ employs a supported ionic liquid membrane. In some embodiments, the membrane separation of $CO_2$ employs a polyetherimide membrane.

In some embodiments, the method further comprises directing the $CO_2$ from the product stream to a methanation reactor that reacts the $CO_2$ to yield a methanation product stream comprising methane. In some embodiments, the method further comprises directing the methane in the methanation product stream to the OCM reactor. In some embodiments, the method further comprises separating the product stream into (i) an ethylene product stream comprising ethylene and (ii) a $C_{3+}$ product stream comprising compounds with three or more carbon atoms ($C_{3+}$ compounds). In some embodiments, the method further comprises directing ethane from the product stream to the OCM reactor. In some embodiments, the method further comprises prior to directing the product stream into the separations unit, compressing the product stream.

In another aspect, the present disclosure provides a method for generating compounds with two or more carbon atoms ($C_{2+}$ compounds), comprising: (a) directing water into an electrolysis unit that electrolyzes the water to yield oxygen ($O_2$) and hydrogen ($H_2$); (b) directing the $O_2$ from the electrolysis unit and methane ($CH_4$) into an oxidative coupling of methane (OCM) reactor that reacts the $O_2$ and $CH_4$ in an OCM process to yield a product stream comprising (i) $C_{2+}$ compounds, including ethylene ($C_2H4$) and (ii) carbon monoxide (CO) and/or carbon dioxide ($CO_2$); (c) directing at least a portion of the CO and/or $CO_2$ from the product stream and the $H_2$ from the electrolysis unit into a methanation reactor that reacts the $H_2$ and the CO and/or $CO_2$ to yield $CH_4$; and (d) directing at least a portion of the $CH_4$ from the methanation reactor to the OCM reactor.

In some embodiments, the electrolysis unit comprises an alkaline water electrolysis system. In some embodiments, the electrolysis unit comprises a proton exchange membrane electrolysis system. In some embodiments, the electrolysis unit comprises a steam electrolysis system.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H4$) and (ii) carbon dioxide ($CO_2$); (b) directing the product stream from the OCM reactor into a separations system that employs a $CO_2$ separation unit that separates the $CO_2$ from the product stream to enrich the $C_{2+}$ compounds in the product stream; and (c) directing at least a portion of the $CO_2$ separated in (b) to the OCM reactor.

In some embodiments, the product stream is directed into the separations system through one or more additional units.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising $C_{2+}$ compounds including ethylene ($C_2H4$) and heat; (b) using an evaporator to transfer at least a portion of the heat from the product stream to an organic working fluid in a closed fluid flow cycle as part of an organic Rankine cycle (ORC) system, to evaporate the organic working fluid, which closed fluid flow cycle includes the evaporator, a turbine, a condenser, and a pump; (c) directing the organic working fluid evaporated in (b) to the turbine to generate power; (d) directing the organic working fluid from the turbine to the condenser that condenses the organic working fluid; and (e) directing the organic working fluid condensed in (d) to the pump.

In some embodiments, the organic working fluid is selected from the group consisting of hydrocarbons, silicon oils, and perfluorocarbons. In some embodiments, a boiling point of the organic working fluid is less than a boiling point of water.

In another aspect, the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H4$) and heat; (b) transferring at least a portion of the heat from the product stream to a thermoelectric power generator; and (c) with the aid of the heat, using the thermoelectric power generator to generate power.

In some embodiments, the thermoelectric generator comprises a thin film thermoelectric module. In some embodiments, the thermoelectric generator comprises a micro thermoelectric module.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

DETAILED DESCRIPTION

Figure 1:
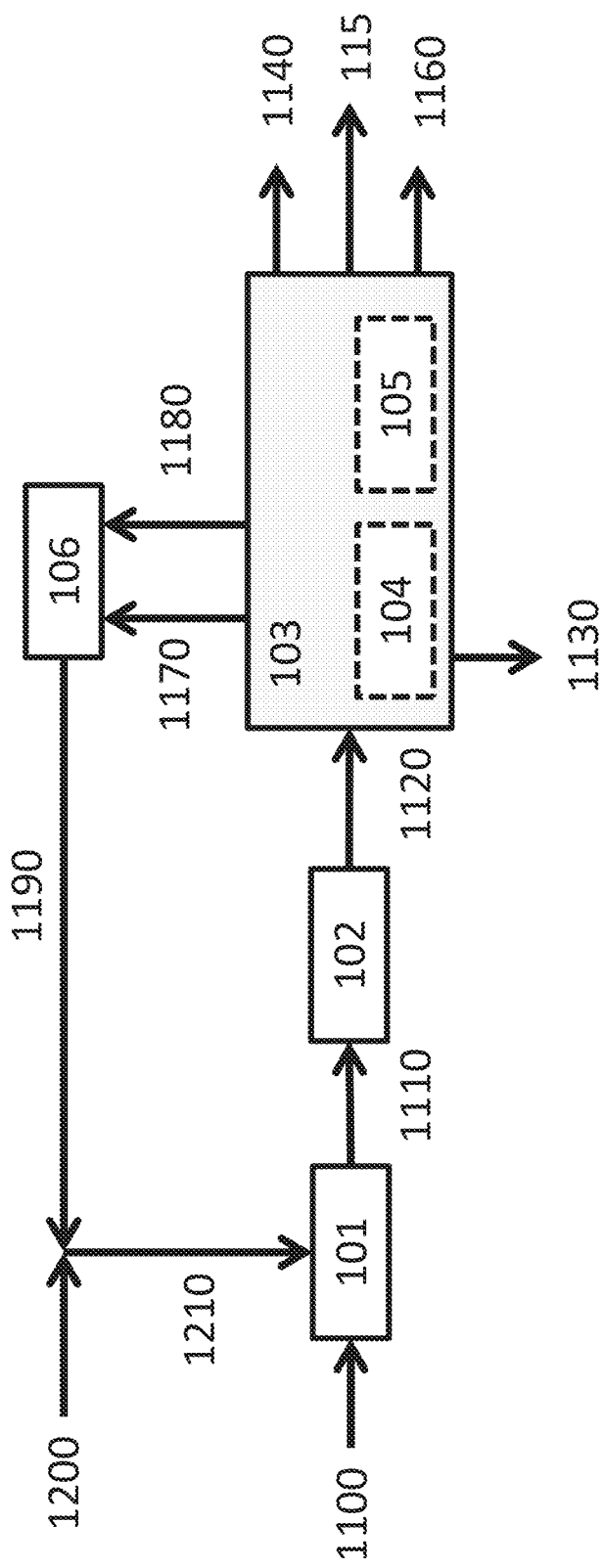
FIG. 1 shows a typical oxidative coupling of methane (OCM) system with advanced separation.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4 + O_2 \rightarrow C_2H_4 + 2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds include, without limitation, alkanes, alkenes, alkynes and aromatics containing two or more carbon atoms. $C_{2+}$ compounds can include aldehydes, ketones, esters and carboxylic acids. Examples of $C_{2+}$ compounds include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1000, 1100, 1200, 1300, 1400, 1500, or 1600 KTA of an olefin.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process. In some cases, power for the operation of the process can be provided by heat liberated by an OCM reaction. In some cases, the systems or methods of the present disclosure have a carbon efficiency of at least about 50%, at least about 55%, at least about 60%, at least about 65%, at least about 70%, at least about 75%, at least about 80%, at least about 85%, or at least about 90%. In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%.

The term "$C_{2+}$ selectivity," as used herein, generally refers to the percentage of the moles of methane that are converted into $C_{2+}$ compounds.

The term "specific oxygen consumption," as used herein, generally refers to the mass (or weight) of oxygen consumed by a process divided by the mass of $C_{2+}$ compounds produced by the process.

The term "specific $CO_2$ emission," as used herein, generally refers to the mass of $CO_2$ emitted from the process divided by the mass of $C_{2+}$ compounds produced by the process.

Separations

Various non-cryogenic separation techniques have been increasingly employed for gas separations, purifications and recovery of hydrocarbons. Membrane based processes and adsorbents have been intensively studied for large scale applications for olefins recovery. Since the development of synthetic adsorbents and pressure swing adsorption (PSA) cycles, adsorption has been playing an increasingly important role in gas separation and purification.

PSA technology can be used in a large variety of applications: Hydrogen purification, air separation, $CO_2$ removal, noble gases purification, methane upgrading, n-iso paraffin separation and so forth. While new applications for gas separations by adsorption are continually being developed, the most important applications have been air separation (for production of $O_2$ and $N_2$) and hydrogen separation (from fuel gas). Approximately 20% of $O_2$ and $N_2$ are currently produced by PSA. The increasing industrial applications for adsorption have stimulated a growing interest in research and new applications.

Processes of the present disclosure can employ a variety of different separations techniques, alone or in combination. For example, OCM processes can employ amine and caustic systems for $CO_2$ removal, molecular sieve guard beds for water removal, and cryogenic distillation or other separation techniques for recovery and purification of hydrocarbon components. Cryogenic separation can refer to separations using temperature levels below 120 K or about −153° C. Other techniques include Selexol™ and Rectisol™ processes for $CO_2$ removal.

OCM product effluent can comprise a mixture of hydrocarbons including but not limited to methane, ethane, ethylene, propane, propylene, butanes, butenes, and higher hydrocarbons. OCM product effluent can also comprise varying amounts of other components such as $H_2$, $N_2$, CO, $CO_2$ and $H_2O$. The product of an OCM reaction can include ethylene. The ethylene product can be polymer grade, refinery grade or chemical grade. Depending on the purity level required, different separation and/or purification techniques can be employed with the OCM process. To recover high purity ethylene, separation methods such as those discussed herein can be used to remove a wide range of components.

Advantages of the advanced OCM processes described herein can include reducing the cost, reducing the number of unit operations ("units") used, and hence improving the overall process for producing high purity polymer grade ethylene. Overall conversion and carbon efficiency can also be improved. The separation methods disclosed herein can also improve the overall conversion and carbon efficiency.

The different separation and purification techniques discussed herein can be used to separate the OCM product effluent (e.g., process gas) into a plurality of streams, including but not limited to a first stream comprising methane, hydrogen, carbon monoxide and other lighter inerts and a second stream comprising ethane, ethylene, propylene, and higher hydrocarbons. Separation systems or subsystems employed can include those discussed herein, such as a cryogenic demethanizer, a membrane separation system, or a PSA based system.

The separation techniques discussed herein can be employed to remove $CO_2$, such as from an OCM product effluent stream. One or more separations techniques can be used to remove $CO_2$ including but not limited to absorption, adsorption, $CO_2$ distillation, and membrane separation. The separation technique can be non-cryogenic.

FIG. 1 shows a block flow diagram for an exemplary OCM process. Oxygen 110 and methane 121 can be fed into an OCM reactor 101 for conversion into higher hydrocarbon compounds including ethylene. The OCM product stream 111 can be directed to a compressor 102, and the compressed product stream 112 can be fed into a separations system 103. The separations system can include pretreatment units 104, such as impurity and $CO_2$ removal units, as well as separations units 105, such as cryogenic, non-cryogenic, complexation, membrane, and other separations units. The separations system can be a combination of more than one separation techniques, such as those discussed in this application. The separation system can replace $CO_2$ removal, moisture removal, and cryogenic separation systems of existing OCM process systems. The compressor system may not be required for some types of separation processes. From the separations system, $CO_2$ can be vented 113, ethane 114 can be recovered, for example for recycling to the OCM reactor, ethylene product 115 can be recovered, and $C_{3+}$ products 116 can be recovered. Additionally, $CO_2$ 117 and methane 118 can be directed from the separations system into a methanation unit 106. The methanation unit can produce methane from the $CO_2$, for recycling 119 back to the OCM reactor. Additional methane 120 can be added to the OCM reactor supply stream 121.

Auto Refrigeration

OCM process systems can use refrigeration subsystems to condense overhead vapors, for example from a demethanizer, a deethanizer, and/or a $C_2$ splitter. The temperatures employed can be in the range from about 12° C. to about −100° C. These low temperatures can be achieved through the use of multiple refrigeration systems, such as ethylene refrigeration and propylene refrigeration systems, to provide different levels of refrigeration. These can be similar to those employed in existing steam crackers.

Figure 2:
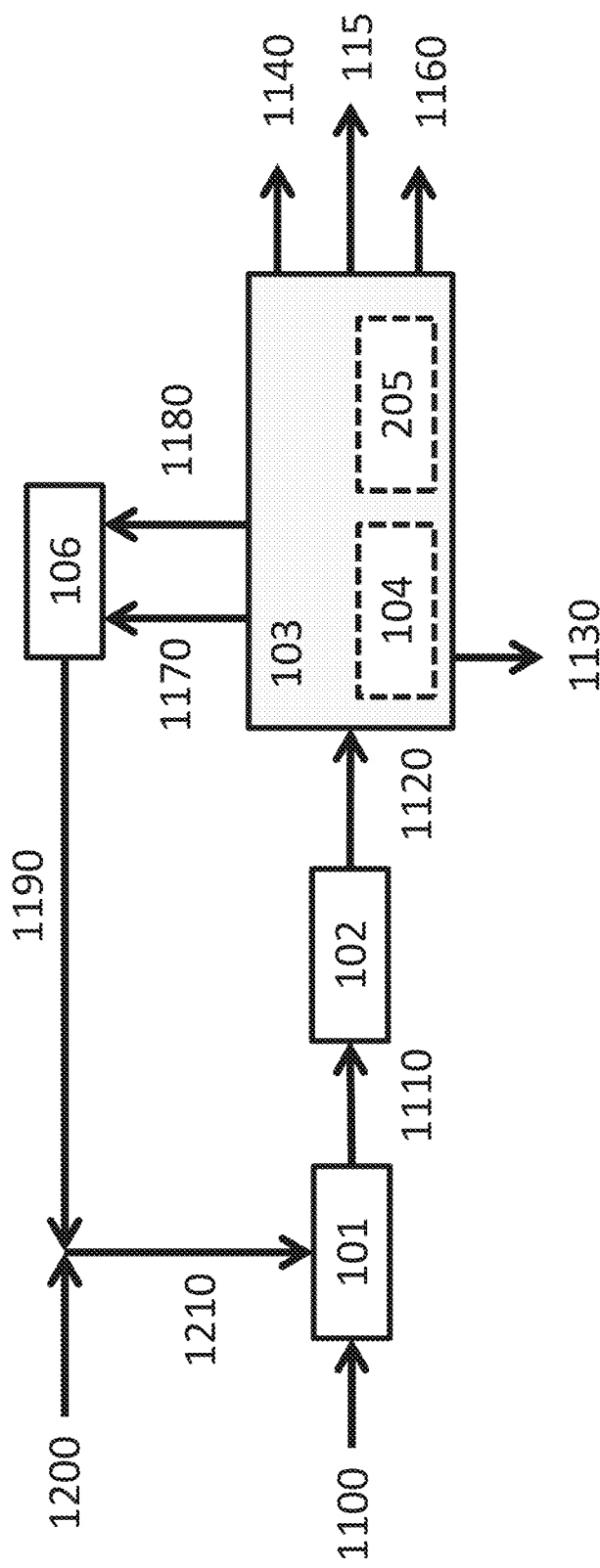
FIG. 2 shows an OCM system with auto refrigeration (e.g., methane refrigeration)

Alternatively, an open loop methane refrigeration system can be employed to provide refrigeration for a demethanizer. OCM product effluent can comprise methane as the major component, for example at a concentration of at least about 50 mol %, 60 mol %, 70 mol %, 80 mol %, or 90 mol %. The demethanizer can have the lowest temperature requirements in the entire separations unit. Use of methane refrigeration (e.g., auto-refrigeration) can provide benefits such as elimination of the need for an additional refrigeration system (e.g., new) for any added capacity. For grassroots or greenfield OCM applications, this can considerably reduce refrigeration compressor sizes needed. In some cases, an entire refrigeration system can be eliminated. FIG. 2 shows a block flow diagram for an exemplary open loop methane refrigeration system, such as can be used in gas processing plants and steam crackers to produce chilling for condensing overhead vapors from a demethanizer. Most elements of FIG. 2 correspond to the description in FIG. 1; the separations unit 205 can include an open loop methane refrigeration system to provide cooling for the separations. The system can be combined with a single or multiple stage (e.g., two-stage) expansion system (e.g., Joule Thompson) to chill the incoming feed. In certain cases, multiple separate lighter products are recovered, such as a light $H_2$-rich stream, a low pressure methane rich stream, and a high pressure methane rich stream.

Mixed Refrigeration

Another alternative to ethylene and propylene refrigeration subsystems is the use of a mixed refrigeration system. The mixed refrigerant can be, for example, a mix of methane, ethylene and propylene. The mixed refrigerant can be a mix of ethane and propane. A wide range of possible mixed refrigerants can be employed, and can be selected based on, for example, the availability of certain components and the degree of refrigeration required. A mixed refrigerant system can provide advantages for use with an OCM reactor system, including the use of only one refrigeration sub system. Rather than two refrigeration systems each comprising multiple stages of refrigerant compressor, associated vessels, exchangers, and other components, the process can use a single refrigeration system. This can substantially reduce capital cost. This can also reduce equipment count, which can be a benefit especially for OCM retrofits at places where plot space may be a concern.

Pi Complexation

Pi complexation techniques can be used to separate alkenes from alkanes. Some metal ions complex selectively with unsaturated organic compounds. Some of these complexes are reversible while others are irreversible. For example, aqueous silver salt in solution forms reversible complexes with olefins, and forms irreversible complexes with acetylenes. This property can be employed in an OCM process to recover ethylene and propylene from OCM reactor effluent.

Figure 3:
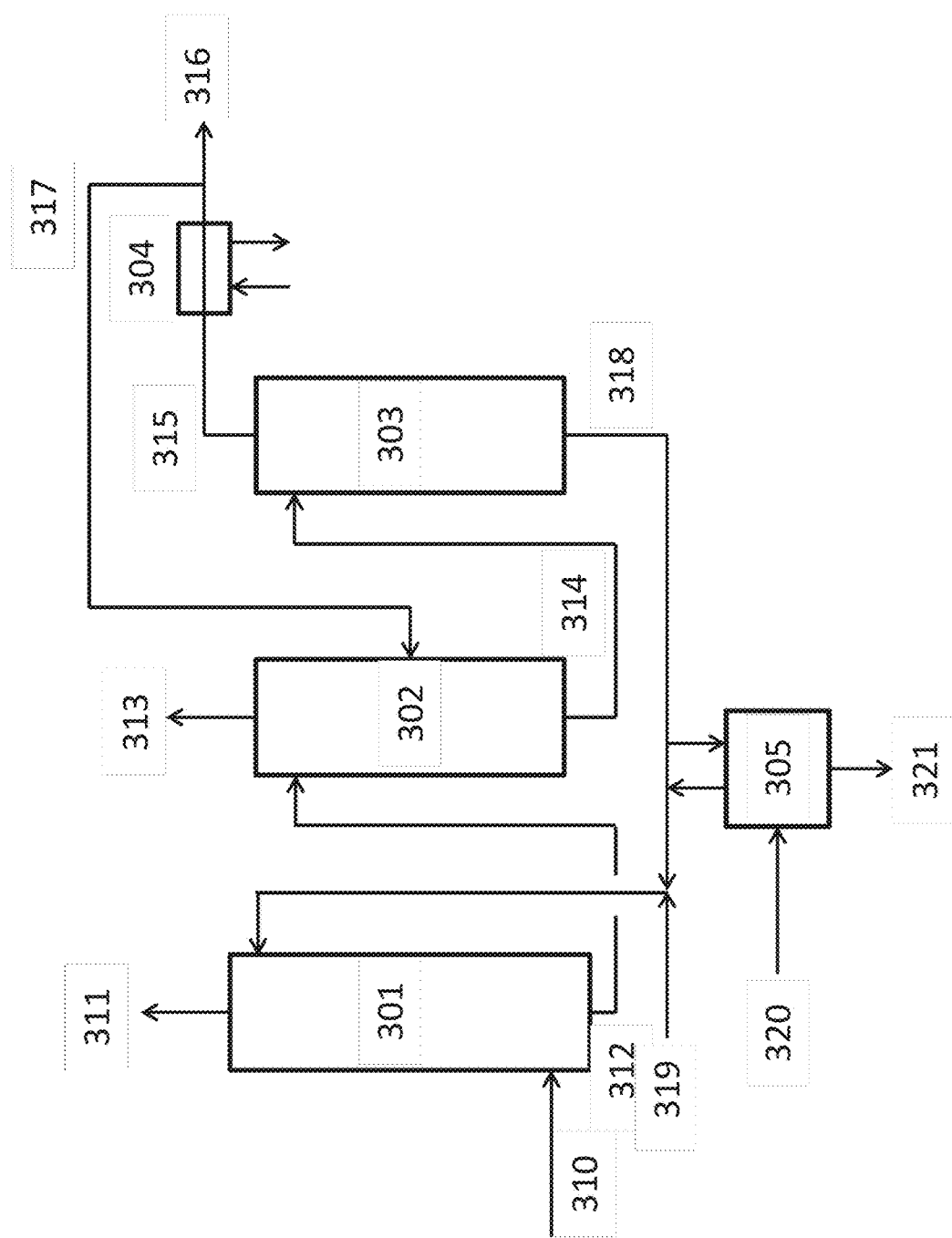
FIG. 3 shows an exemplary OCM system with a silver complexation ethylene recovery subsystem.

As shown in FIG. 3, separation of ethylene and/or propylene by metal complexation can be divided into three major sections: absorption, purification or venting of impurities, and desorption. An exemplary process is provided for separation of ethylene and/or propylene from a purified multi-component gas stream from the OCM reactor. FIG. 3 shows a process for purifying a stream containing ethylene using an aqueous silver nitrate solution. Metal complexation (e.g., silver or cuprous ion complexation) can be used to separate ethylene and/or propylene from a purified multi-component gas stream produced via OCM comprising $C_2$ compounds, $C_3$ compounds, and lighter components such as hydrogen and nitrogen. First, the multi-component gas stream 310 can be introduced into an absorber 301 with aqueous silver salt solution, such that the ethylene and/or propylene undergo absorption or complexing with the silver metal ions, and such that trace acetylenes react with the silver metal ions. Vent gas 311 can be removed from the absorber. Then, the silver salt solution stream 312 can be vented 313 in a vent column 302 at reduced pressure to remove any dissolved low molecular weight components. Then, the resulting silver salt solution stream can be treated in a stripper 303 to separate the absorbed or complexed ethylene and/or propylene from the silver salt solution, and further treated in a treatment unit 304 to release the trace acetylenes. Purified ethylene 316 can be recovered, and some product can be recycled 317. The aqueous silver salt stream 318 can then be recycled to the first step, in some cases after regeneration in a regeneration unit 305 with $AgMnO_4$ 320. $MnO_2$ 321 can be removed from the regeneration unit. $H_2O_2$ 319 can be added to the solvent stream being returned to the absorber.

Useful adsorbents include but are not limited to metal compounds, such as silver or copper, supported on high surface area carriers with a plurality of pores. These adsorbents can be used in pressure swing adsorption or temperature swing adsorption processes. When operating pressure and/or temperature is changed, the silver or copper compound can release the alkene-rich component from the adsorbent. These adsorbents can be very effective for selective adsorption of alkenes such as ethylene, propylene, and mixtures of these from gaseous mixtures.

When a gaseous component solubilizes in a liquid and complexes with its ions, the loading of the gas can be affected by its partial pressure and the temperature and the concentration of the complexing ions in the solution. Therefore, by changing the physical conditions separately or collectively, the active gaseous component can either be formed into or out of the solution. Adjusting or swinging one or more physical parameters can be used to carry out an ethylene or propylene separation using an aqueous silver nitrate solution. Purification or venting of impurities can result in a product stream that is free or substantially free of impurities including but not limited to $CO_2$, sulfur compounds, acetylenes, and hydrogen. Acetylene and hydrogen can cause operational problems and so the process gas can be treated to bring the concentration of such impurities to within an acceptable limit.

Metal complexation can be used in combination with other processes, such as membrane based processes.

Membranes

Membranes can be used to perform a variety of separations, such as separations of olefins and paraffins, or separations of $CO_2$. A membrane can be essentially a barrier that separates two phases and restricts transport of various chemicals in a selective manner. Polymer membranes can be used to separate mixtures such as propylene/propane mixtures and ethylene/butene mixtures. Separations in polymeric membranes are dependent on the solubility and diffusion of the species through the membrane. While zeolite-based separations are predominantly depended on molecular size differences, the differing permeation of olefins through a polymeric membrane can be largely attributed to differences in solubility, which can depend on the critical temperature and the kinetic diameter. Membrane separations can be employed even when there are small molecular size differences.

The OCM process can utilize a membrane based separation process to further enhance the efficiency and energy consumption of the process. Cryogenic distillation can be used for the separation of alkenes, but is highly energy intensive. Membrane based separations can be used for a variety of purposes in the context of an OCM process, such as to separate and purify ethylene product from OCM reactor effluent, to separate a stream rich in $CO_2$, to separate a stream containing lighter hydrocarbons and inerts, or to separate $C_2$ compounds from $C_1$ and lighter compounds.

Membranes can include but are not limited to isotropic membranes, anisotropic membranes, and electrically charged membranes. A membrane can be a ceramic membrane, a metal membrane, or a liquid membrane. An isotropic membrane can be a microporous membrane or a nonporous dense membrane. Membranes can be used for separations including but not limited to $CO_2$ separation, paraffin-olefin separation, or selective recovery of pure ethylene from the OCM reactor effluent. Polymer derived carbon molecular sieve membranes can be used to separate paraffins from olefins. These membranes can be used, for example, to separate ethylene from a mix of methane and ethane.

Membrane separations can be used in combination with other types of separation and purification subsystems to remove other impurities such as acid gases, hydrogen, and nitrogen.

Transport through a membrane can take place when a driving force is applied to the components in the feed. A driving force can be a pressure differential or a concentration (activity) gradient across the membrane. Membrane based separation techniques can be used in an OCM process by applying either of the above mentioned driving forces. A membrane based separation can also be a component of a hybrid separation set-up, such as a membrane and an absorption system (e.g., a membrane contactor) or a membrane in a pressure swing adsorption (PSA) or a temperature swing adsorption (TSA) system.

An OCM reactor can employ membranes as a part of the reactor system to effectively separate the ethylene product within the reactor system itself. A section of the reactor can include membranes that aid in recovering the ethylene product, with a methane rich stream being recycled to a methanation system and eventually to the OCM reactor. Such a system can also use advanced heat recovery or quench methods so as to facilitate the use of membranes.

Pressure Swing Adsorption (PSA) and Adsorption Technology

Cryogenic separation (e.g., distillation) can be used for the recovery of ethylene, propylene, and other components from olefin plants, refinery gas streams, and other sources. These separations can be difficult to accomplish because of the close relative volatilities, and can have significant temperature and pressure requirements for operation. The ethane/ethylene distillation can be performed at about −25° C. and 320 pounds per square inch gauge (psig) in a column containing over 100 trays. Distillation of propane and propylene can be performed at about −30° C. and 30 psig. These can be some of the most energy intensive distillations in the chemical and petrochemical industry. In general, the use of distillation towers to separate recover and purify components is an energy intensive process.

The present disclosure provides the use of adsorbents that can achieve separation and purification of olefin rich streams. In particular, the present disclosure applies the use of PSA-based adsorbent systems to separate, purify, and recover olefins like ethylene and propylene from streams containing one or more impurities such as methane, hydrogen, carbon monoxide, carbon dioxide, ethane, or others. The streams, or parts of the streams, can be generated via an OCM process, an ETL process, or combinations thereof. The streams can be final product streams where PSA is used to recover and purify the final product. The streams can be intermediate streams which are purified prior to use as a feed in a subsequent process, such as an ETL process, an ethylene cracker (steam cracker), a refining unit, a fuel gas system, a natural gas recovery plant or any other product fractionation or product treatment unit.

Pressure Swing Adsorption (PSA)

A pressure swing adsorption (PSA) process cycle is one in which desorption takes place at a different (e.g., lower) pressure than the adsorption pressure. Reduction of pressure can be used to shift the adsorption equilibrium and affect regeneration of the adsorbent. Low pressure may not be as effective as temperature elevation in totally reversing adsorption, unless very high feed to purge pressure ratios are applied. Therefore, most PSA cycles are characterized by high residual loadings and thus low operating loadings. These low capacities at high concentration require that cycle times be short for reasonably sized beds (e.g., seconds to minutes). These short cycle times are attainable because particles of adsorbent respond quickly to changes in pressure. Major uses for PSA processes include purification as well as applications where contaminants are present at high concentrations.

Figure 4:
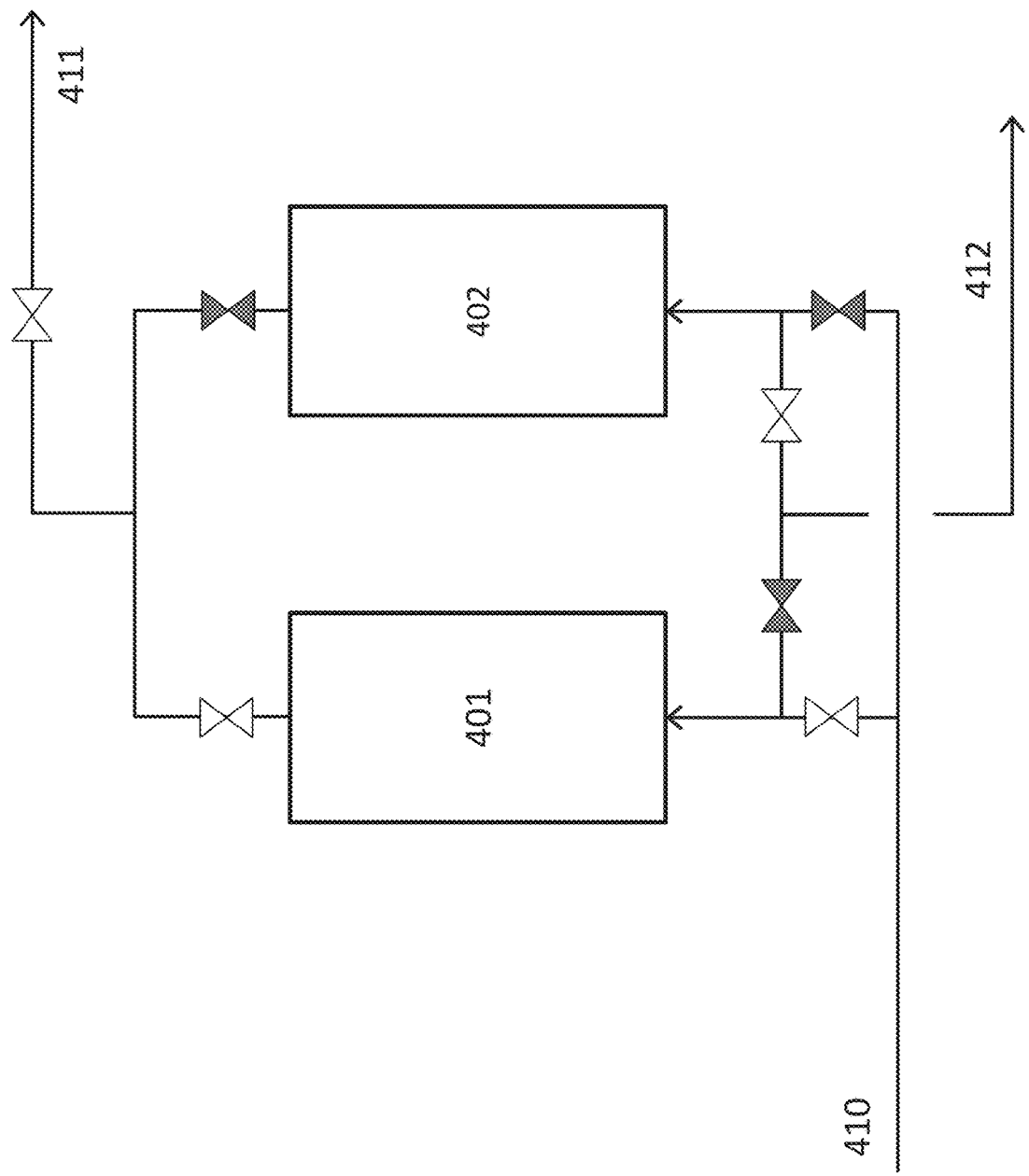
FIG. 4 shows an exemplary pressure swing adsoprtion (PSA) system.

As shown in FIG. 4, the PSA system can comprise two fixed bed adsorbers 401 and 402 undergoing a cyclic operation of four steps—adsorption, blowdown, purge, and pressurization. The PSA system can receive a feed 410 and produce a product stream 411, with a PSA off gas stream 412. For improving the performance of the basic Skarstrom™ cycle (FIG. 4), additional operation steps can be employed such as pressure equalization, product pressurization, and co-current depressurization. Besides these steps, the number of beds can be modified to achieve the optimal operation and multi-bed processes can be used in commercial applications like hydrogen recovery. Similarly, a TSA system can be used where a swing in temperature causes the sorption and desorption.

PSA cycles are used primarily for purification of wet gases and of hydrogen. High pressure hydrogen employed in processes such as hydrogenation, hydrocracking, and ammonia and methanol production can be produced by PSA beds compounded of activated carbon, zeolites and carbon molecular sieves. Other exemplary applications include: air separation, methane enrichment, iso/normal separations, and recovery of CO and $CO_2$.

Adsorbents

Adsorbents can be natural or synthetic materials, such as those having amorphous or microcrystalline structure. Exemplary adsorbents useful for large scale operation include but are not limited to activated carbon, molecular sieves, silica gels, and activated alumina. Other useful adsorbents include pi complexation sorbents, silver and copper complexation adsorbents, zeolites, synthetic zeolites, mesoporous materials, activated carbons, high surface area coordination polymers, molecular sieves, carbon molecular sieves (CMS), silica gels, MCM, activated alumina, carbon nanotubes, pillared clays, and polymeric resins.

For systems where the incoming stream is a multi-component mixture of gases and the number of compounds to be separated cannot be removed by a single adsorbent, different layers of adsorbents can be used. For example, hydrogen purification from a methane stream in a reforming operation, where $H_2$ is contaminated with $H_2O$, $CO_2$, CO, and unconverted $CH_4$, can employ activated carbon to remove $H_2O$ and $CO_2$ in combination with additional layers of adsorbents used to increase the loading of CO.

Zeolites, molecular sieves, and carbon molecular sieves (CMS) can be used for most industrial separations employing PSA. Inorganic materials, like special kinds of titanosilicates, can be used for kinetic separations.

For systems specifically configured to separate ethane/ethylene and propane/propylene, exemplary types of adsorbents include zeolites/molecular sieves and pi complexation sorbents. Zeolites/molecular sieves can be used for kinetic separation, such as separation based on higher diffusivity of olefins over that of paraffins. The use of 4 A zeolite is one such example. Pi complexation sorbents, such as $AgNO_3$/$SiO_2$, can give excellent results as compared to 4 A zeolite. PSA units as discussed herein can employ a range of different sorbents, including but not limited to a zeolite/molecular sieve sorbent, a pi complexation based sorbent, a carbon molecular sieve sorbent or any other form of activated carbon, carbon nanotubes, polymeric resin based sorbents, or other sorbents.

Adsorbents can be selected based on a number of different criteria. Adsorbent selection criteria can include capacity for the target components (e.g., affinity for the desired components to be separated from the multi-component feed stream), selectivity between components competing for same adsorption sites, regenerability of the adsorbent, (e.g., the ability of the adsorbent to release the adsorbed target components at a reasonable pressure rate of gas diffusion into the adsorbent—this can also affect the size of the bead that is chosen and consequently the pressure drop across the bed; an insufficient diffusion rate can require smaller diameter beads that can result in higher pressure drop and hence increased operating costs), and chemical compatibility (e.g., selecting an adsorbent resistant to chemical attack that may poison or destroy the adsorbent, such as liquid hydrocarbons causing physical breakdown of the adsorbent resulting in loss of efficiency and back pressure).

$CO_2$ Separation

Figure 5A:
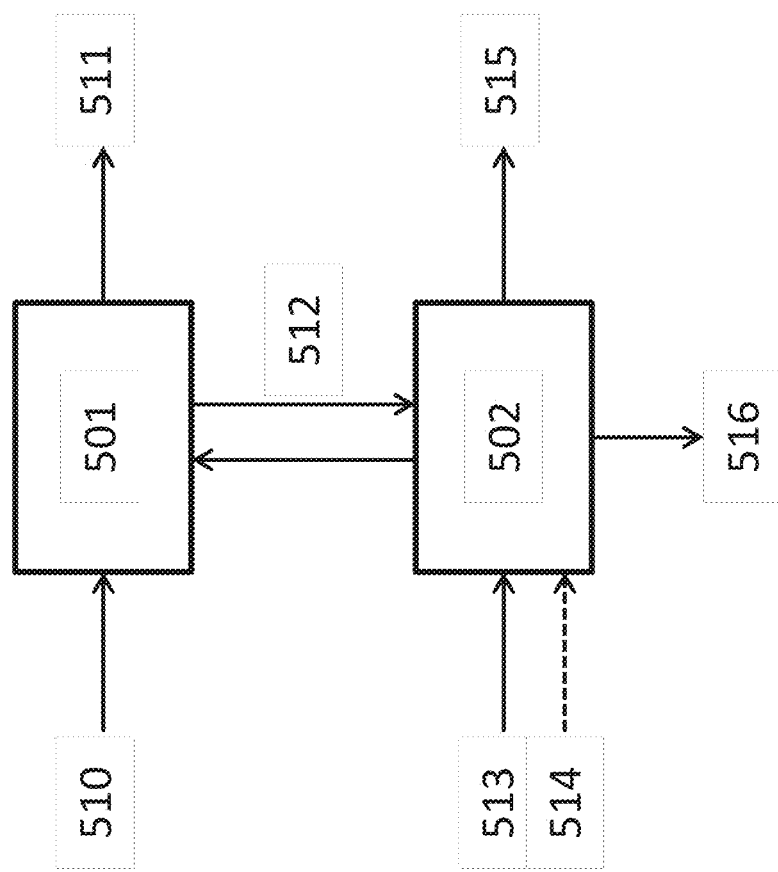
FIG. 5A shows a schematic of $CO_2$ separation methods.
Figure 5B:
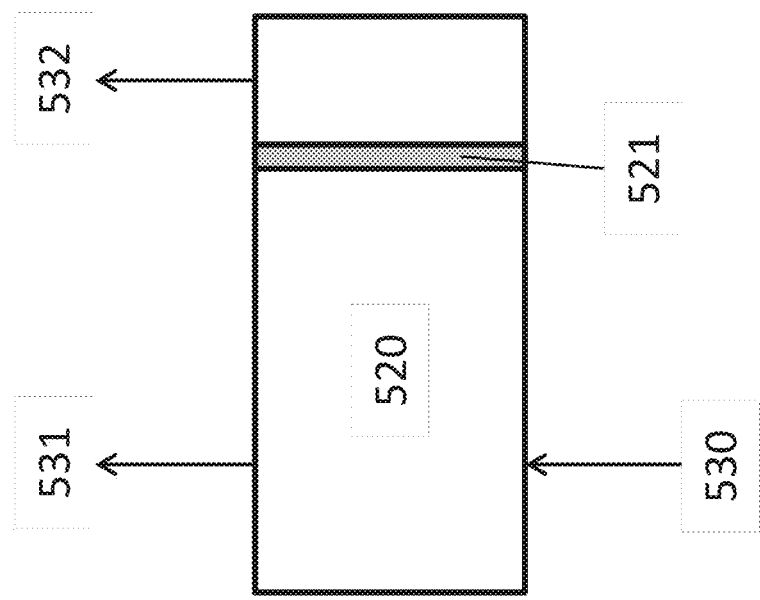
FIG. 5B shows a schematic of $CO_2$ separation methods.
Figure 5C:
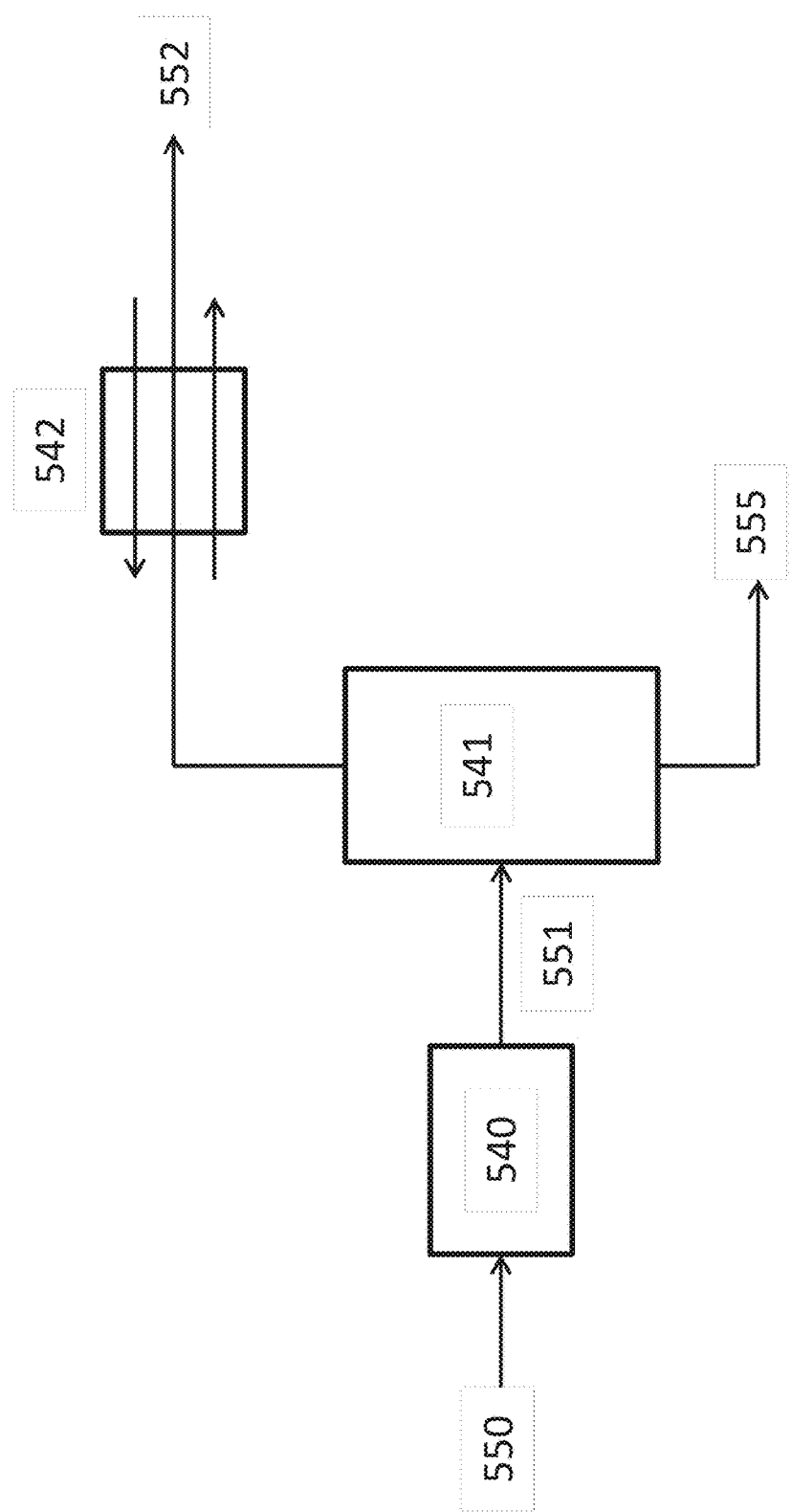
FIG. 5C shows a schematic of $CO_2$ separation methods.

There are many technologies available for $CO_2$ capture, such as from flue gases, natural gas, or from any process gas rich in $CO_2$. Various processes for post-combustion or pre-combustion capture can be used reduce $CO_2$ emissions. FIG. 5A, FIG. 5B, and FIG. 5C show exemplary schematics of different separation methods available to separate $CO_2$ from a process gas or a flue gas.

OCM processes can utilize an amine based absorption system for $CO_2$ removal, which can be followed by use of a caustic scrubber to obtain high degree of separation. The amine system is prone to corrosion, solvent degradation, and above all, has high energy requirements. Separations with sorbents and/or solvents can involve placing the $CO_2$ containing gas in intimate contact with a liquid absorbent or a solid sorbent that is capable of capturing the $CO_2$. As shown in FIG. 5A, a stream with $CO_2$ 510 can be directed into a capture vessel 501, where it contacts sorbent which captures $CO_2$ from the stream. The stream, with reduced or removed $CO_2$, can then exit 511 the vessel. Sorbent 512 loaded with captured $CO_2$ can be transferred to a sorbent regeneration vessel 502 where it releases the $CO_2$ after being heated (e.g., with the use of energy 513), after a pressure decrease, or after any other change in the conditions around the sorbent, thereby regenerating the sorbent. Spent sorbent 515 and $CO_2$ 516 can be removed from the vessel, and make up sorbent 513 can be added. After the regeneration step the sorbent can be sent back to capture more $CO_2$ in a cyclic process. The sorbent can be a solid. Solid sorbent can remain in a single vessel rather than being cycled between vessels; sorption and regeneration can be achieved by cyclic changes (e.g., in pressure or temperature) in the vessel where the sorbent is contained. A make-up flow of fresh sorbent can be used to compensate for natural loss of activity and/or sorbent losses.

Amine scrubbing technology can be used to remove acid gases from process gases. Primary amines (e.g., MEA, DGA), secondary amines (e.g., DEA, DIPA), tertiary (e.g., MDEA, TEA), sterically hindered amines, chilled ammonia, potassium carbonate, and other compounds can be used to remove $CO_2$ from process gases. Traditional amine based systems can be characterized by high energy requirements and solvent degradation. Improved solvents, which can require less energy for regeneration of the solution, include the Benfield process and two stage diethanolamine. Combination with an OCM process can reduce the energy consumption of amine scrubbing processes. Improved solvents can reduce the energy requirements by as much as 40% compared to the traditional MEA solvents. This has the potential of reducing the energy, and hence steam, consumption of the OCM process, thereby increasing the amount of steam available for export from the OCM, or making alternative waste heat recovery methods feasible.

Physical absorption solvents used can include but are not limited to glycol dimethylethers (e.g., Selexol) and propylene carbonate (e.g., IPTS/EC). Regeneration of the solution can be performed by vacuum flashing and air stripping; this approach can consume significantly less energy than in chemical absorption. In using physical solvents $CO_2$ can be released mainly by depressurization, thereby avoiding the high heat of consumption of amine scrubbing processes.

Mixed or hybrid solvents can include but are not limited to Sulfinol™ (sulfolane, water, and amine), such as Sulfinol-M and Sulfinol-X.

Solid adsorbents, such as zeolites and activated carbon, can be used to separate $CO_2$ from gas mixtures. In pressure swing adsorption (PSA), a gas mixture can flow through a packed bed of adsorbent at elevated pressure until the concentration of the desired gas approaches equilibrium. The bed can be regenerated by reducing the pressure. In temperature swing adsorption (TSA), the adsorbent can be regenerated by raising its temperature. In general usage, adsorption is not yet considered attractive for large scale separation of $CO_2$ because the capacity and $CO_2$ selectivity of available adsorbents are low. However, when the OCM process is a recycle process, an adsorbent based separation method can be used to separate bulk $CO_2$ followed by consuming the remaining $CO_2$ in a methanation reactor system, or by using a caustic scrubber to treat the remaining $CO_2$.

Many different types of membrane materials (e.g., polymeric, metallic, ceramic) can be used for $CO_2$ capture to preferentially separate $CO_2$ from a range of process streams. FIG. 5B shows an exemplary schematic of separation of $CO_2$ from a gas stream 530 in a separation vessel 520 using a membrane 521. $CO_2$ can be removed from the stream via the membrane, and $CO_2$ and other gases can exit the vessel in separate streams 531 and 532. The main limitation of currently existing membranes is the occurrence of severe plasticization of the membrane in the presence of high pressure $CO_2$. Due to excessive swelling of the polymer membrane upon exposure to $CO_2$, the performance (e.g., selectivity) can decrease significantly, thus reducing the purity of the $CO_2$ and consequently reducing the possibilities for reuse of the gas. Energy requirements can be significantly lower for membrane based technologies; for example, membrane technology can use 70-75 kWh per ton of recovered $CO_2$ compared to significantly higher values for pressure swing adsorption (e.g., 160-180 kWh), cryogenic distillation (e.g., 600-800 kWh), or amine absorption (e.g., 330-340 kWh), making membrane technology an attractive option for integration with OCM for $CO_2$ separation.

Membrane and amine technologies can be combined to form a hybrid process to capture $CO_2$. Micro-porous hollow fiber membranes can be used for $CO_2$ separation using amine-based chemical absorption processes. Micro-porous membranes can be used in a gas-liquid unit where the amine solution is contacted with $CO_2$ containing gas. Using the membrane can lead to a reduction in the physical size and weight of the gas-liquid contacting unit. The separation is based on reversible chemical reaction, and mass transfer occurs by diffusion of the gas through the gas/liquid interface as in traditional contacting columns. Such a hybrid membrane contactor can provide a high contact area between gas and liquid, reduce or essentially eliminate foaming and flooding problems, and give better operational flexibility while reducing solvent degradation problems.

A membrane contactor can combine the advantages of membrane technology and solvent absorption for $CO_2$ separation. A membrane contactor is a combination of advanced membrane techniques with an effective absorption process. A membrane contactor is a hybrid mass exchanger where a porous membrane separates two phases. The selective sorbent performs the separation while the membrane facilitates the mass exchange process by expanding the phase contact surface area. The modified surface properties can improve the selectivity of the process by selectively inhibiting the transport of one of the mixture constituents. Compared to a conventional column device, membranes can allow for up to five times increase in yield per unit volume. Since the sorptive liquid flows within capillaries and both phases are not directly contacting each other, membrane absorbers can operate in any spatial configuration (horizontal or vertical) and at any flux rations between both phases. Also, there is no flooding or uneven packing moisturization. Since the system operates with unchanging yields, independent of the diameter and height; scaling up is fairly simple. Membranes used can be micromembranes or ultrafiltration membranes made a variety of different polymer and ceramic materials. Polypropylene fiber membranes can be used to separate $CO_2$ from $CH_4$, for example by using amines like MEA as absorption liquid. Hollow fiber membranes, such as porous polypropylene, perfluoroalkoxy (PFS), and asymmetric poly (phenylene oxide) hollow fiber membranes with a dense ultrathin skin at the outside of the membrane can also be used. Besides amines as absorption liquid, other absorption liquids may be used, such as aqueous sarcosine salt solutions, for example in a gas-liquid membrane contactor system. A membrane contactor can be used to separate the $CO_2$ from the OCM effluent in which $CH_4$ is the major component. Membrane contactors can also be used for separation of olefins and paraffins, and the separation of $CO_2$ from light gases.

An activator, such as piperazine, diethanolamine, and arsenic trioxide, can be used to further enhance the effectiveness of $CO_2$ capture. DGA and tertiary amines may provide more improvement than primary or secondary amines.

Gas selective poly ionic liquid membranes, which are polymerized room temperature ionic liquids (RTIL), can be used to be highly selectively separate $CO_2$. RTILs can be synthesized as a monomer and subsequently polymerized to obtain gas selective membranes. The ionic nature of the polymers can result in tight arrangements between the oppositely charged ionic domains in the poly RTIL, which can eventually prevent the membrane from excessive swelling and deterioration of its performance at increased pressure and/or temperature. This intrinsic property of poly RTIL can be used to increase the resistance against plasticization and to restrict strong swelling of the polymer membrane to maintain its permeation properties in the presence of a strong plasticizing agent such as $CO_2$ at higher pressures. For example, an imidazolium-based poly RTIL can be used as base material and the length of the alkyl chain can serves to strengthen or weaken the ionic interactions within the poly RTIL. High pressure mixed $CO_2$/$CH_4$ gas separation measurements at different temperatures.

Gas components like $CO_2$, from $N_2$ or $CH_4$ can be separated with supported ionic liquid membranes. Ionic liquids are molten salts with a very low melting point (many are liquids at room temperature). Many ionic liquids show a high solubility for carbon dioxide and hence can be highly suitable for use with an OCM process. For example, ionic liquids can include but are not limited to imidazolium, pyrollidinium, pyridinium, cuanidinium, phosphonium, morpholinium, piperidinium, sulfonium, ammonium, hexafluorophosphate, tetraflouroborate, alkylsulphate, triflate, dicyanamide, bis(trifluoromethylsulfonyl)imide, and combinations thereof. Specific advantages of ionic liquids include very low to negligible vapor pressure, good dissolution characteristics for many substances, and lack of flammability or toxicity. Ionic liquids can have good thermal, mechanical and chemical stability as well as favorable densities and viscosities. The required specifications can be adjusted easily by the large number of possible combinations of anions and cations when formulating an ionic liquid. Ionic liquids can be used as chemical solvents, catalysts, electrolytes in fuel cells as well as for gas-separation and storage by absorption. Ionic liquid membrane systems can comprise an adequate porous support material, e.g. a polymer film, coated by ionic liquids. The system separated $CO_2$ and sulfur compounds from different gas mixtures. Competitive selectivity and permeability are obtained for the separations. Novel membrane materials, such as polyetherimides, can be used as membrane material with improved plasticization resistance for $CO_2$ removal, for example with an OCM process. Other membrane materials that can be used include polymeric membranes based on polyamides, polysemicarbazides, polycarbonates, polyarylates, polyaniline, poly(phenylen oxide), polysulfones, and polypyrrolones. In some cases, the polymeric membrane is solvent resistant and can reduce the plasticization effects of hydrocarbons in the feed stream, e.g., polyketone, polyether ketone, polyarylene ether ketone, polyimide, polyetherimide, and polyphenylene sulphide, which have intrinsic solvent inertness and can therefore withstand organic rich operation conditions.

An adequate porous support material, e.g. a polymer film, coated by ionic liquids can be used in continuous separation of $CO_2$ and sulfur compounds from different gas mixtures, including a methane rich stream. This separation can improve the efficiency of OCM processes. The OCM reactor effluent can enter the supported ionic liquid separation subsystem, and $CO_2$ and other contaminants can be removed from the process gas. Other contaminants can include but are not limited to traces of sulfur compounds, inerts, CO, $SO_2$, $H_2S$, and tetrahydrothiophene (THT).

$CO_2$ can be separated from other gases by cooling and condensation, for example as shown in FIG. 5C. A stream containing $CO_2$ 550 can be compressed in a compressor 540, and the compressed stream 551 can be directed to a distillation column 541. Some components can be recovered from the overhead stream 552, with heat recovered in a heat exchanger 542. Other components can be recovered from the bottoms 555. Cryogenic separation is widely used commercially for streams that already have a high concentration of $CO_2$ (typically greater than 90%). Cryogenic separation of $CO_2$ has the advantage that it enables direct production of high purity liquid $CO_2$ that can be used as a feedstock to convert the carbon to higher value hydrocarbons, or otherwise be captured. The amount of energy required can be high, and water may need to be removed before the feed gas is cooled.

Low temperature distillation can give better results when there is a high concentration of $CO_2$ in the feed gas. For the OCM process gas, the $CO_2$ concentration can be increased by, for example, having a recycle stream, or by using a modified OCM reactor where excess $CO_2$ is used as a quench medium for the reaction heat. Low temperature separation can refer to separations using temperature levels above −90° C.

Figure 6:
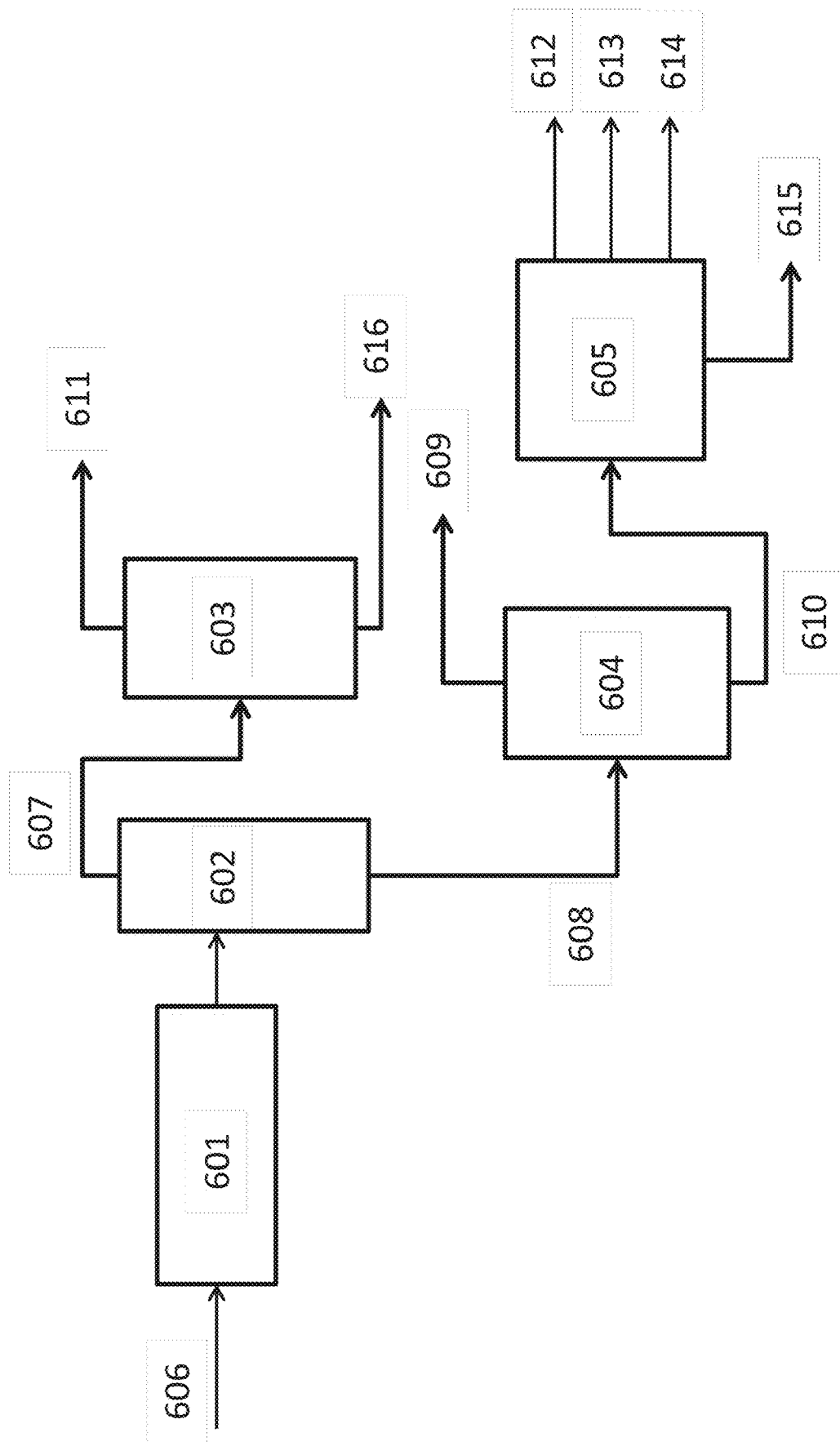
FIG. 6 shows typical $CO_2$ distillation system.

FIG. 6 shows a schematic of $CO_2$ separation using distillation. OCM reactor effluent 606 can be fed to a treatment unit 601, such as a molecular sieve dryer, a sulfur removal bed, or an acetylene removal bed. The treated gas is fed to the first distillation column 602 that separates the bulk of the methane from the $CO_2$ and other heavier hydrocarbons. Depending on the $CO_2$ concentration in the stream 606, the bottom stream 608 may contain 50%, 60%, 70%, 80%, 90% (or anywhere in between) of the incoming $CO_2$. The overhead from 607 contains majority of the methane and other light gases and is fed to the column 603. Column 603 further recovers methane rich gas 611, which can be the feed to a methanation system. The bottoms product 616 may be recycled or sent as a purge to the fuel gas system. The $CO_2$ rich gas 608 is distilled in the $CO_2$ column 604 to recover pure $CO_2$ 609 in the overhead. The bottoms product 610 can contain some methane along with ethane, ethylene, and other heavier hydrocarbons, and can be sent to recover the ethylene product in a separator 605. The $CO_2$ product can be sent to methanation unit, and a part of the $CO_2$ can be recycled to achieve the desired concentration of $CO_2$ in the feed stream 606. Such a $CO_2$ distillation sub system can offer many benefits, including but not limited to reducing the loop size of the OCM process considerably, as the function of the existing cryogenic demethanizer can be reduced by a large extent. Additionally, amine and caustic systems can be replaced by cryogenic or low temperature distillation systems.

Alkaline salt-based processes can be used for carbon dioxide removal. These processes can utilize the alkali salts of various weak acids, such as sodium carbonate and potassium carbonate. These processes can provide advantages such as low cost and minimal solvent degradation. Processes that can be used for $H_2S$ and $CO_2$ absorption include those using aqueous solutions of sodium or potassium compounds. For example, potassium carbonate can absorb $CO_2$ at high temperatures, an advantage over amine-based solvents.

Hot potassium carbonate ($K_2CO_3$) solutions can be used for the removal of $CO_2$ from high-pressure gas streams, among other applications. Potassium carbonate has a low rate of reaction. To improve $CO_2$ absorption, mass transfer promoters such as piperazine, diethanolamine, and arsenic trioxide can be used. Less toxic promoters such as borate can also be used, for example with flue gas streams (see, e.g., Ghosh et al., "Absorption of carbon dioxide into aqueous potassium carbonate promoted by boric acid", Energy Procedia, pages 1075-1081, February 2009, which is hereby incorporated by reference in its entirety). To limit corrosion, inhibitors can be added. These systems can be known as activated hot potassium carbonate systems. Licensed hot activated potassium carbonate systems include the Benfield™ and the Catacarb™ process. The processes can be used for bulk $CO_2$ removal from high-pressure streams, but can also produce high-purity $CO_2$.

Flue gas impurities such as SOx and NOx can reduce the operational efficiency of the potassium carbonate as a solvent. $SO_2$ and $NO_2$ may not able to be released from the solvent under industrial conditions. Selective precipitation of the impurity salts formed by SOx and NOx can be used to remove such compounds (see, e.g., Smith et al., "Recent developments in solvent absorption technologies at the CO2CRC in Australia" Energy Procedia, pages 1549-1555, February 2009, which is hereby incorporated by reference in its entirety).

A variety of materials can be used as $CO_2$ sorbents through chemical reactions and physical absorptions, including but not limited to soda-lime, active carbon, zeolites, molecular sieves, alkali metal oxides, silver oxide, lithium oxide, lithium silicate, carbonates, silica gel, alumina, amine solid sorbents, metal organic frameworks and others.

Physical impregnation of $CO_2$-reactive polymers, such as tetraethylene pentamine or polyethyleneimine, inside a porous support, such as alumina, pumice, clay or activated carbon, can be used for $CO_2$ removal. Amine based sorbents can be easily regenerated. Alternatively, a mixture of an amine compound with a polyol compound can be impregnated in a porous support. The polyol compound can be used to increase the $CO_2$ desorption rate of the amine. The supported amine-polyol sorbent can comprise from about 1 wt % to about 25 wt % amine and from about 1 wt % to about 25 wt % polyol, with the balance being the support. Solid sorbent can adsorb and desorb $CO_2$ a relatively high rates at ambient temperatures. Enhanced $CO_2$ cyclic removal capacities in either dry or humid air flows can further be achieved by using a solid sorbent at an increased amine concentration of amines from about 35 wt % to about 75 wt %.

Solid sorbents that can selectively remove multiple gases can be used to remove $CO_2$, $H_2O$, nitrogen oxides, and hydrocarbons. This can be achieved by using composite adsorbents, for example by using a mixed adsorbent of alumina and zeolite to remove $CO_2$ and $H_2O$ simultaneously.

$CO_2$ can be separated from flue gas using an ion pump method instead of relying on large temperature and pressure changes to remove $CO_2$ from a solvent. Ion pump methods can dramatically increase the overlying vapor pressure of $CO_2$. As a result, the $CO_2$ can be removed from the downstream side of the ion pump as a pure gas. The ion pumping can be obtained from techniques including but not limited to reverse osmosis, electro dialysis, thermal desalination methods, or an ion pump system having an oscillation flow in synchronization with an induced electric field.

By making use of energy such as renewable or nuclear energy, carbon dioxide and water can be recycled into sustainable hydrocarbon fuels in a non-biological process. Various pathways can enable such a conversion, for example by $H_2O$ and $CO_2$ dissociation followed by fuel synthesis. The methods of dissociation can include heat, electricity, and solar driven methods such as thermolysis, thermochemical loops, electrolysis, and photoelectrolysis. High temperature electrolysis can make efficient use of electricity and heat, provide high reaction rates, and integrate well with fuel synthesis.

Synthetic analogues of enzymes as a polymer thin film supported on micro-porous substrates can be used to separate $CO_2$ from gas mixtures. For example, a polymer thin film containing carbonic anhydrase mimicking sites can supported on a porous substrate and can separate $CO_2$ from a stream containing $O_2$ and $N_2$. The system can be, for example, about 30% lower in cost compared to amine-based systems.

Process Configurations
Electrolysis to Generate Oxygen and Hydrogen for OCM Process Electrolysis can be used to produce industrial hydrogen. OCM processes can have a lot of synergistic benefit from deploying a water electrolysis subsystem with the OCM process. The water electrolysis unit can replace an air separation unit (ASU) to supply the oxygen required for the OCM process. The products from the electrolytic unit can be consumed within the OCM process: oxygen can be consumed within the OCM reactor and hydrogen can be used in a methanation reactor. Availability of more hydrogen in the methanation unit has the potential to increase the carbon efficiency to about 100%, by converting the $CO_2$ produced in the OCM reaction to methane, which can be recycled back to the OCM reactor. The OCM unit can be a net exporter of high purity excess hydrogen, after consuming the entirety of the $CO_2$ produced in the OCM Process.

The water electrolysis subsystem can be an electrolytic cell employing alkaline water electrolysis, a proton exchange membrane electrolysis system, or a steam electrolysis system. The electricity source to the electrolytic sub system can be renewable, such as photo voltaic/solar power, which can make the entire system 100% carbon efficient with a zero carbon footprint. A storage system for oxygen, or a backup power supply, may be used to ensure the continuous supply of oxygen and hydrogen.

With steam electrolysis, a substantial part of the energy needed for the electrolysis process can be added as heat, which can be much cheaper than electric energy, and which the OCM reactor can produce in abundance. Therefore, integration of steam electrolysis can take advantage of the extra heat from the OCM reactor to provide energy for the steam electrolysis. This can be of particular benefit to OCM deployments where no additional steam or power is required.

Figure 7:
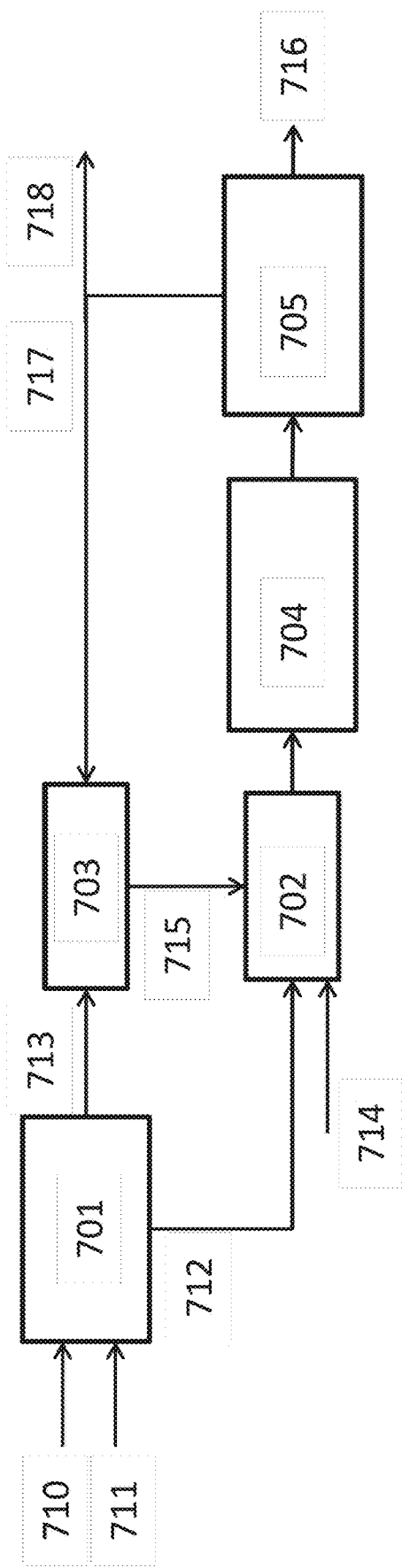
FIG. 7 shows a water electrolysis sub system.

FIG. 7 depicts an exemplary electrolysis subsystem combined with an OCM system. The electrolysis subsystem 701 can take water 710 and electric power 711 as inputs and generate pure oxygen 712 and hydrogen 713 as products. The oxygen can be fed into an OCM reactor 702 with a methane feed 714, for conversion to higher hydrocarbon products including ethylene. The OCM product stream can be compressed in a compressor 704 and separated in a separations unit 705. Higher hydrocarbon products 716 can be recovered from the separations unit, and other compounds such as methane and $CO_2$ can be recycled 717 and/or purged 718. The recycle stream can be directed to a methanation unit 703, which can generate methane 715 using the hydrogen from the electrolysis subsystem. The extra hydrogen that is now available to the methanation unit can enable the conversion of most or all of the $CO_2$ produced in the OCM process to methane, which can drive the process to a higher efficiency. The process can also be almost 100% emission free. The $CO_2$ produced in the process that may be discarded as waste may be converted to methane and hence to ethylene in the OCM reactor.

Different Quench Media for the OCM Reaction

Figure 8:
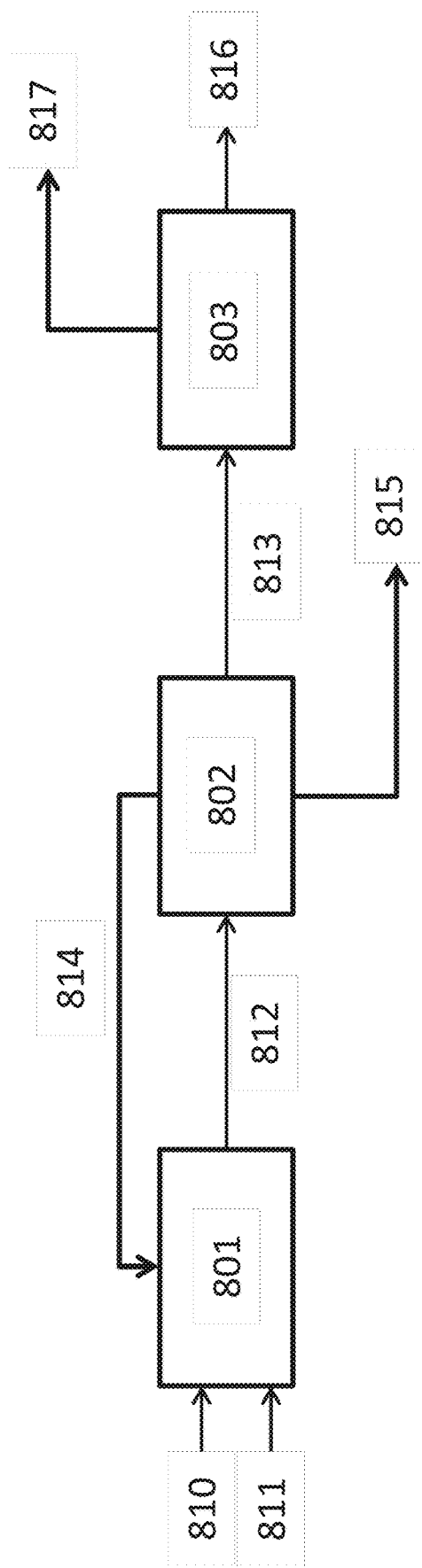
FIG. 8 shows an OCM system with $CO_2$ as a quench medium.

The OCM reaction is highly exothermic. Various quenching media can be used to extract the OCM reaction heat. For example, $CO_2$ can be injected to extract the heat, which results in the OCM effluent containing excess $CO_2$; such effluent can be suitable for the advanced $CO_2$ recovery methods described herein. FIG. 8 shows an exemplary system where $CO_2$ 814 is removed from an OCM product stream 812 (generated in an OCM unit 801 from an oxygen stream 810 and a methane stream 811) in a $CO_2$ separation unit 802 and recycled from back to the OCM reactor 801. A waste gas or purge stream 815 can also be removed from the $CO_2$ separation unit. The OCM product stream 813 can then be separated in a separations unit 803 into a product stream 816 comprising ethylene and a purge and/or recycle stream 817. Separation methods can include low temperature separation, membrane separation, or other separation methods discussed herein. The OCM loop can be decreased to just a $CO_2$ recycle stream. The system can also comprise a methanation unit (not shown).

Such an approach can provide advantages including a smaller recycle loop and more efficient $CO_2$ removal methods, resulting in lower capital expenditure (CAPEX). This can also result in the feasibility of small distributed scale OCM units, since after the removal of excess $CO_2$, the relatively richer ethylene stream needs fewer treatment and recovery steps.

Heat Recovery

Waste heat from the OCM process can be used to generate superheated high pressure steam that can be used in the process, exported to other users on site, or can be used to generate power. Excess process heat can also be used to preheat the feed streams. Other uses for excess heat can be less capital intensive, and offer a greater operational flexibility and low maintenance. Thermoelectric energy conversion can be used to convert waste heat to power. Example uses for waste heat include single fluid rankine cycles (e.g., steam cycle, hydrocarbons, and ammonia), binary/mixed fluid cycles (e.g., ammonia/water or mixed hydrocarbon cycle).

Organic Rankine Cycle

The organic Rankine cycle (ORC) can be used to generate power from heat. In ORC, an organic component is used instead of water. The organic compound can be a refrigerant, a hydrocarbon (e.g., butane, pentane, hexane), silicon oil, or a perfluorocarbon. The boiling point of the organic fluid can be lower than that of water, which can allow recovering heat at a lower temperature than in the traditional steam Rankine cycle.

Owing to the exothermicity of the OCM reaction, the ORC system can be deployed as a waste heat recovery method for use with OCM. Waste heat at relatively low temperature can be recovered by an intermediate heat transfer loop and used to evaporate the working fluid of the ORC.

Figure 9:
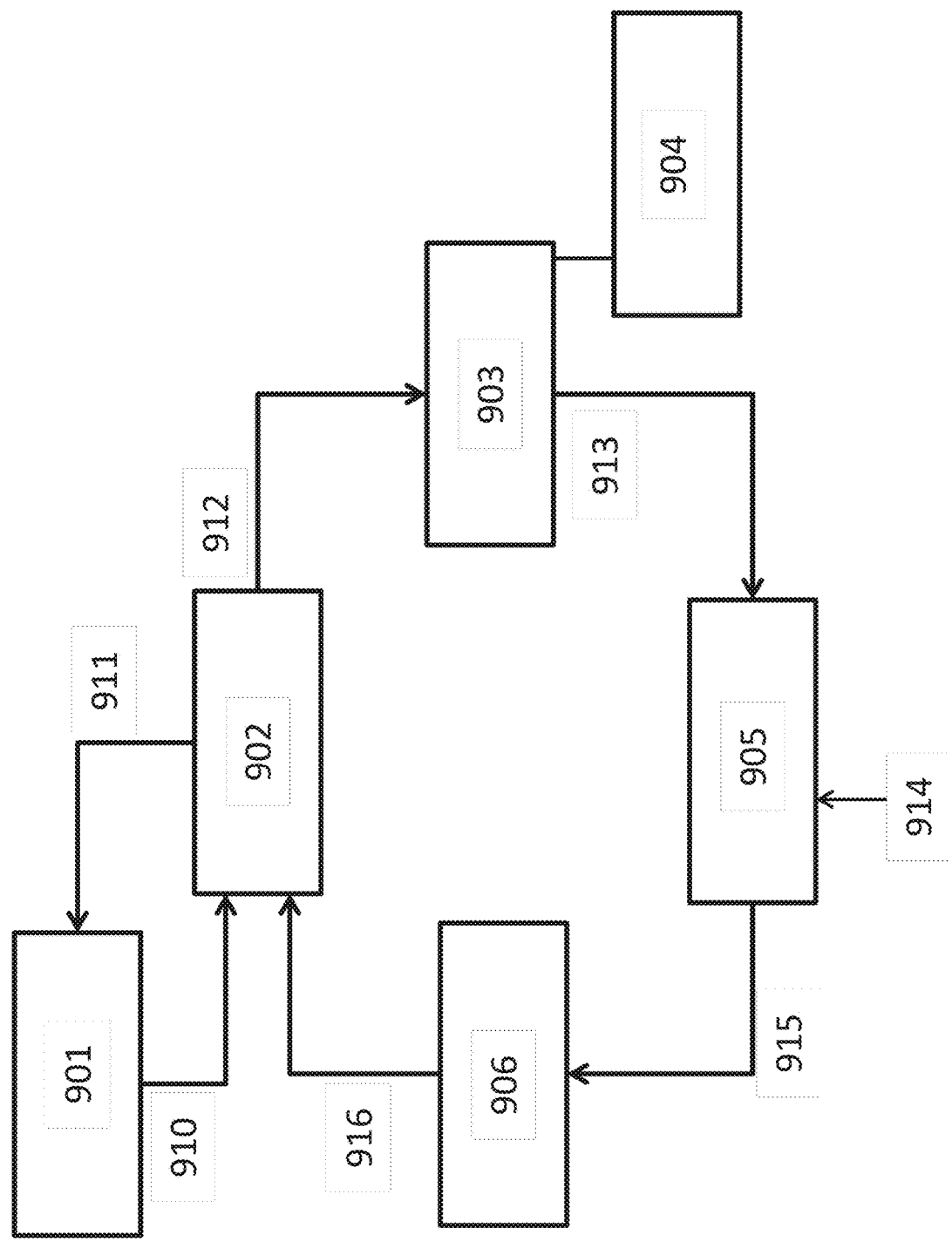
FIG. 9 shows an organic Rankine cycle (ORC) subsystem.

FIG. 9 shows an exemplary OCM system with an ORC subsystem. The working fluid can be chosen which can be condensed with cooling water or air at normal atmospheric pressure. FIG. 9 shows the heat source as the OCM reaction heat from an OCM unit 901. Heat can be recovered from the OCM product stream 910 in an evaporator 902, and the product stream 911 can then be directed for downstream processing from the OCM unit. The heat recovered in the evaporator can be used to evaporate a working fluid stream 912, which can then be directed to a turbine 903 to generate power in a generator 904. From the turbine, the working fluid 913 can be directed to a condenser 905 and cooled using a cooling medium 914. The cooled working fluid 915 can then be pumped by a pump 906 in a stream 916 back to the evaporator.

Thermoelectric Power Generation

The OCM process can make use of a heat exchanger with thermoelectric (TE) generators for heat recovery. A Thermoelectric Power Generator (TPG) can have four basic components: Heat source, P and N type semiconductor stack (or a TE module), heat sink (cold side), and an electrical load (output voltage). The TE module can include two or more of P-type and N-type semiconductor pellets connected in series or parallel depending on the served load.

The TE devices can be solid state engines that do not require any working fluid. Thermoelectric materials can provide efficiencies of up to 15% or greater. Thermoelectric generators coupled with heat exchangers can produce electricity even at temperatures as low as 350 K with low maintenance. TE modules can be used with OCM including large bulk TE modules and thin film or micro TE modules.

For high temperatures, micro TE modules can be used. Micro TE modules can also have low equipment weights. TE devices can be very reliable, scalable, and modular. Some TE modules can give best results at small scales. The OCM process can generate medium level waste heat that is highly suitable for a TE device to generate power.

OCM and ETL Systems with Advanced Separations Sub-Systems

PSA technology can be applied to processes including those involving a hydrocarbon stream containing a mix of the following hydrogen, carbon dioxide, carbon monoxide, methane, ethane, ethylene, propane, propylene, butanes, butenes and/or other higher hydrocarbons needing to be purified or separated into desirable products (e.g., ethylene, methane, hydrogen, or propylene).

Hydrocarbon streams can be produced via traditional refining and petrochemical processes. Hydrocarbon streams can be produced from OCM or ETL reactor systems.

The present disclosure provides the use of PSA in processes and systems for oxidative coupling of methane (OCM) and ethylene-to-liquids (ETL) operations, and the application of adsorbent based processes used in conjunction with OCM and ETL processes to generate significant process improvements and enhance the economic value of the processes. OCM systems are described in, for example, U.S. patent application Ser. No. 14/592,668, which is entirely incorporated herein by reference. ETL systems are described in, for example, U.S. patent application Ser. No. 14/591,850, which is entirely incorporated herein by reference.

Figure 10:
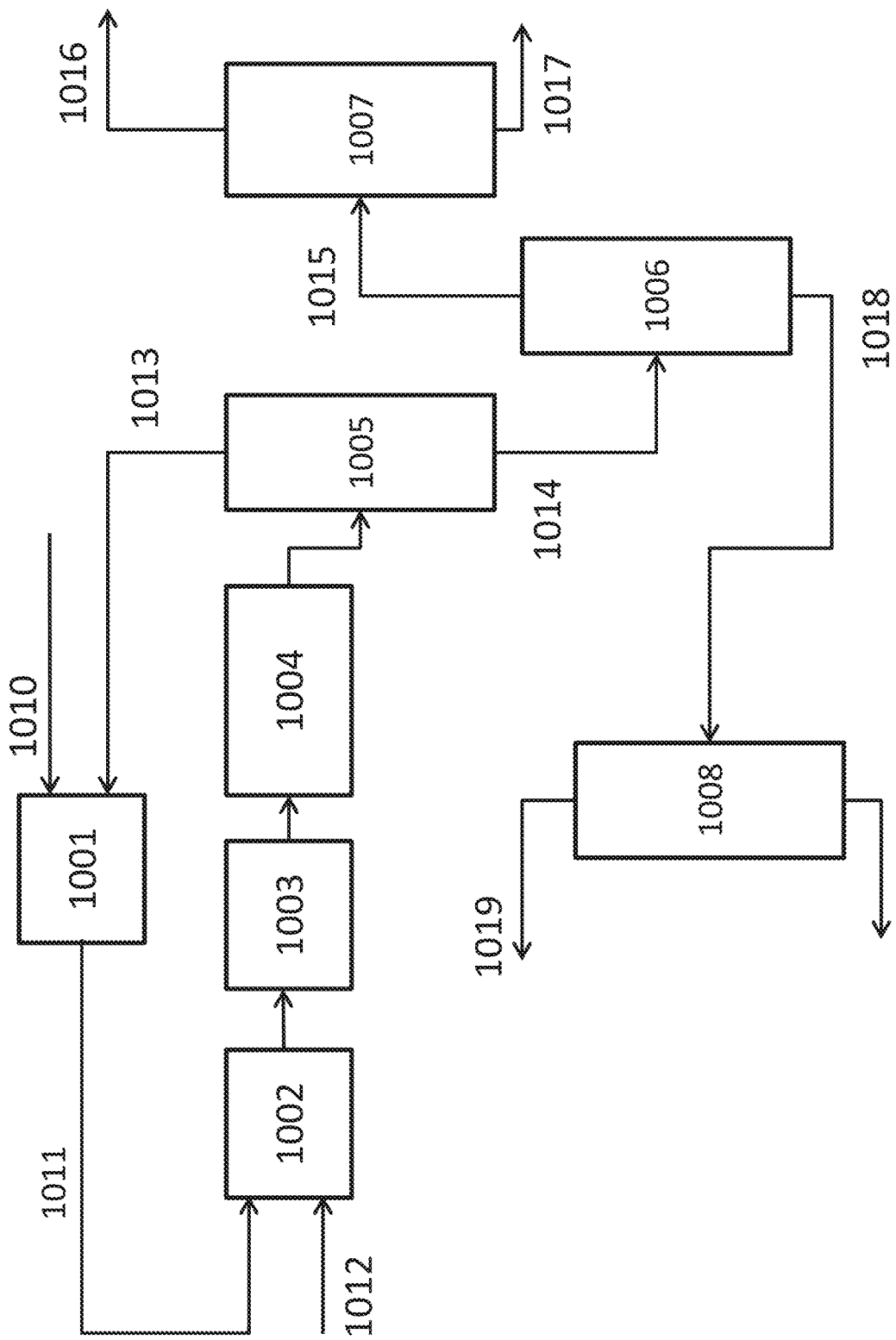
FIG. 10 shows an exemplary typical OCM system.

An OCM system, such as that shown in FIG. 10, can include an OCM or OCM-post-bed-cracking (PBC) reactor 1002, a process gas compression system 1003, a process gas treatment system 1004, a cryogenic separations system, and a methanation system 1001. The feed to the OCM system can be an oxygen feed 1012 and a methane source feed 1011 (such as a natural gas feed stream or other methane source). In some cases, additional ethane feed can be supplied to the PBC section of the OCM reactor, where paraffins such as ethane in the OCM product stream and/or additional ethane can be cracked to olefins such as ethylene. The separations sub-system can comprise a series of fractionation towers, like a demethanizer 1005, deethanizer 1006, $C_2$ splitter 1007, depropanizer 1008, debutanizer, and others. Overhead 1013 from the demethanizer can be directed into the methanation system along with hydrogen or natural gas 1010 to produce additional methane. The bottoms stream 1014 from the demethanizer can be directed to the deethanizer. The overhead stream 1015 from the deethanizer can be directed to the $C_2$ splitter, and there split into ethylene 1016 and ethane 1017 streams. The bottoms stream 1018 from the deethanizer can be directed to the depropanizer, and there split into a $C_3$ product stream 1019 and a $C_{4+}$ product stream 1020. The cryogenic separations system can comprise additional ethylene and propylene refrigeration sub-systems to provide for the chilling requirements of the system.

OCM Process Standalone with Advanced Separations Systems

Figure 11:
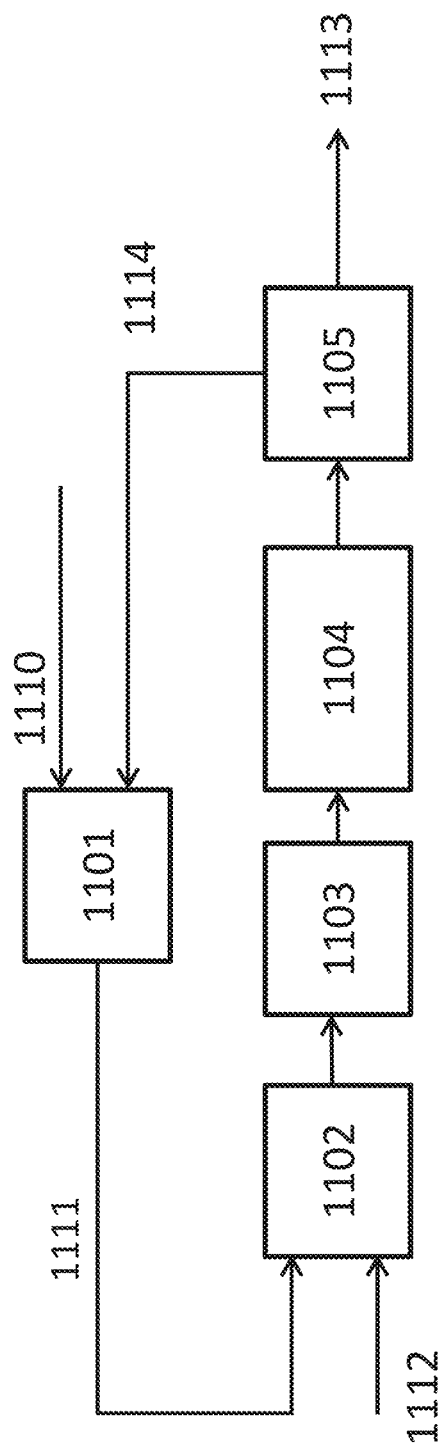
FIG. 11 shows an exemplary OCM system with a single stage PSA unit.

In certain cases, the separations section of the OCM system can be eliminated, or partially eliminated, by utilizing an advanced separations method as discussed in this application. The advanced separation method can be a PSA unit or a membrane based method, or a cryogenic system. FIG. 11 shows an exemplary schematic of OCM with a PSA unit. The PSA unit can separate methane, $CO_2$, CO, and/or $H_2$ from ethane, ethylene, propane, propylene, and/or higher hydrocarbons. Methane 1111 and oxygen 1112 can be directed into an OCM reactor 1102 and reacted to produce higher hydrocarbon products including ethylene. The OCM product can be compressed in a process gas compression system 1103, treated in a process gas treatment system 1104, and separated in the PSA 1105 into a product stream 1113 and a recycle stream 1114. The recycle stream can be directed to a methanation unit 1101, which can also receive a natural gas stream 1110 and produce methane for the OCM reactor. The extent of separation and degree of recovery can depend on the type of adsorbent(s), pressure differential, and number of PSA stages employed. The feed to the PSA unit can have one or more of the following components: $H_2$, $N_2$, $O_2$, CO, $CO_2$, $CH_4$, ethane, ethylene, acetylene, propane, propylene, butanes, butenes, butadiene, water, and higher paraffinic and olefinic components. The PSA product gas can comprise components including but not limited to: $H_2$, $N_2$, CO, $CO_2$, $CH_4$, $O_2$, ethane, ethylene and acetylene. PSA product gas can comprise components from 0% to 99.99% recovery. The PSA tail gas can comprise 99.99%, 90%, 80%, 70%, 60%, 50% ethylene. The PSA tail gas can comprise at least 99.99%, 90%, 80%, 70%, 60%, 50% ethylene. The PSA tail gas can comprise about 99%, 90%, 80%, 70%, 60%, 50%, 40%, 30%, 20%, 10%, 0% ethane. The PSA tail gas can comprise at least about 99%, 90%, 80%, 70%, 60%, 50%, 40%, 30%, 20%, 10%, 0% ethane. The PSA tail gas can comprise about 60%, 50%, 40%, 30%, 20%, 10%, 0% methane, hydrogen, acetylene, $N_2$, $O_2$, $H_2O$ or $CO_2$. The PSA tail gas can comprise at least about 60%, 50%, 40%, 30%, 20%, 10%, 0% methane, hydrogen, acetylene, $N_2$, $O_2$, $H_2O$ or $CO_2$. Based on the process configuration, including the type of adsorbents employed, pressure differential and the operation, various different recoveries are possible.

As discussed above, the PSA unit can comprise one or more adsorbent materials that can be suitable to achieve the component recoveries. The sorbent can be a zeolite/molecular sieve based material, a carbon based sorbent, or a n-complexation sorbent. In some cases the sorbent material can be a polymeric resin, carbon nanotubes, and carbon fibers. The PSA unit can be configured to have layers of different sorbents so as to result in high recoveries from the multi-component feed streams to the desired products.

Figure 12:
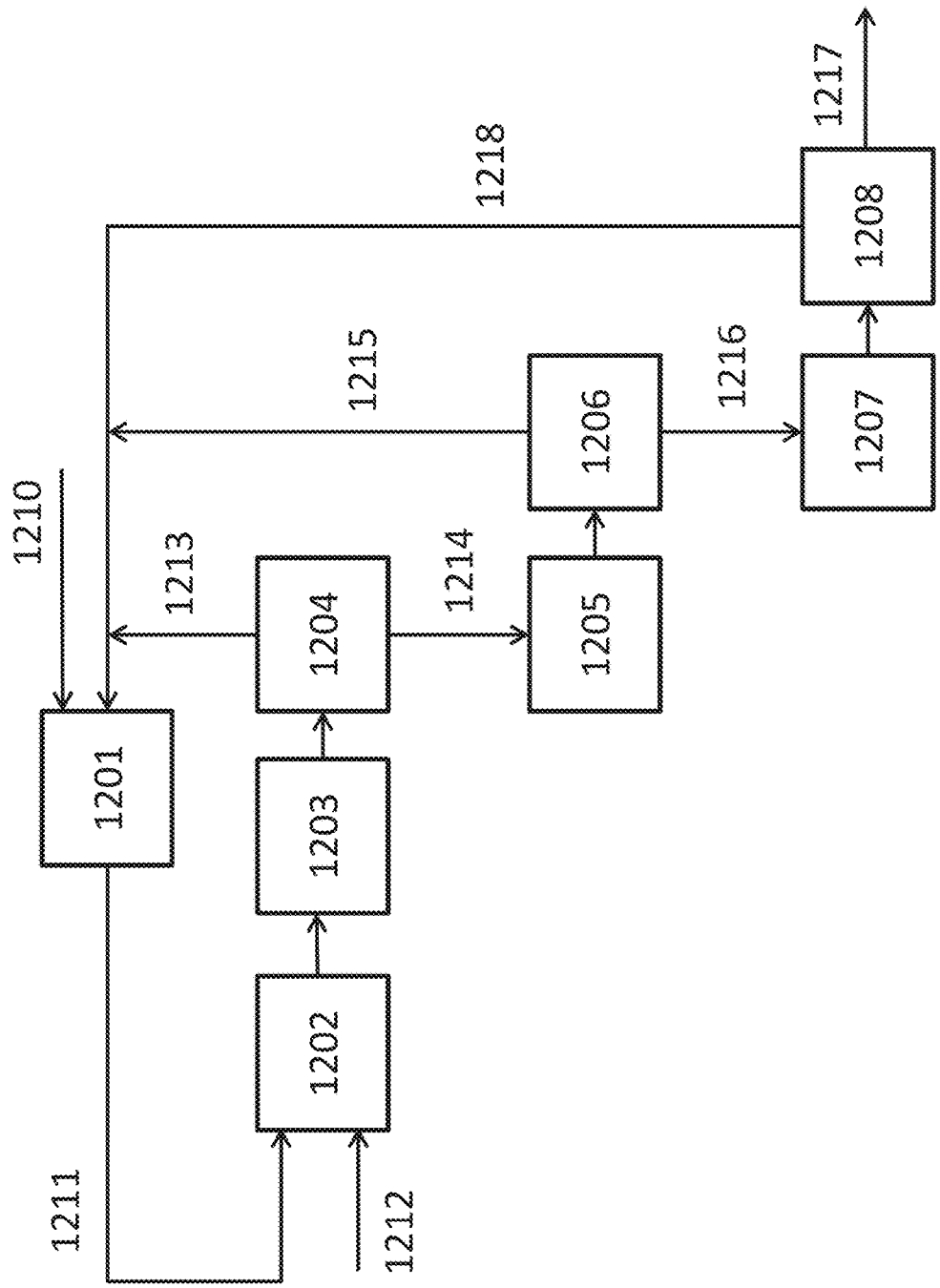
FIG. 12 shows an exemplary OCM system with a multi stage PSA unit.

In certain cases the PSA can be a multi stage unit (see, e.g., FIG. 12). In such a unit, an OCM reactor 1202 can receive a methane stream 1211 and an oxygen stream 1212, and react the methane and oxygen to produce higher hydrocarbon products including ethylene in an OCM product stream. The OCM product stream can be compressed in a first compressor 1203 and directed to a first PSA separation 1204. The tail gas 1214 from the first PSA can be compressed in a second compressor 1205 and fed to a second PSA separation 1206, the tail gas 1216 from which can be compressed in a third compressor 1207 and separated in a third PSA separation 1208. The tail gas from the third PSA can be the final purified stream 1217 containing ethylene up to 99.9% purity. PSA product streams 1213, 1215, and 1218 can be directed to recycle, such as via a methanation unit 1201 along with a natural gas stream 1210. Each PSA stage can be a dual-bed PSA or a multi-bed PSA system.

In certain cases, the process requirements can dictate that only a limited amount of recovery is required in the PSA unit and subsequent recovery and purification is performed in a fractionation column or the gas is a feed for a downstream process unit. The downstream process unit can be an ETL system, an ethylene steam cracker system, a gas processing plant, NGL extraction plant, a refinery off-gas separations system, or other process unit.

Retrofits for OCM

OCM can be employed to convert a feedstock comprising methane to ethylene and other olefins. Historically, ethylene has been produced via steam cracking of gaseous or liquid hydrocarbon feedstocks like ethane, propane, LPG, or naphtha. As in most of the refining and petrochemical operations, a steam cracking operation can involve a cryogenic fractionation or a separations section that consists of a series of fractionation columns to successively recover various components at high product purity.

The present disclosure includes the application of PSA processes to an OCM retrofit of an existing ethylene cracker (e.g., steam cracker).

Figure 13:
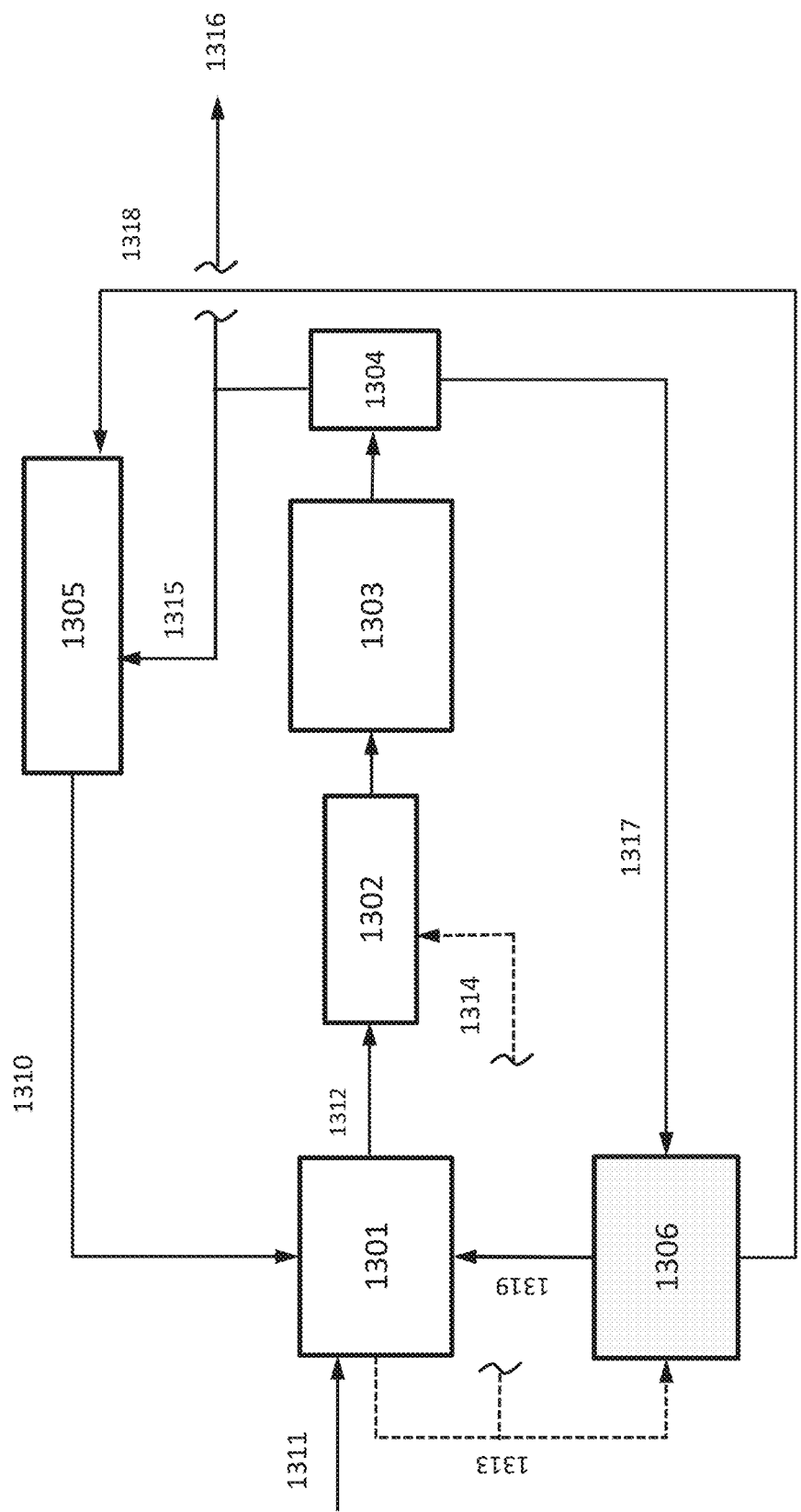
FIG. 13 shows an exemplary retrofit of OCM to a cracker, with a single stage PSA unit.

An example application for OCM combined with a PSA unit involves an existing petrochemical plant such as a steam cracker is considering low cost ways to add ethylene capacity. A typical revamp to add capacity could include addition of, or debottlenecking of, the existing fractionation towers for the entire flow addition for the revamp. However, as shown in FIG. 13, the use of a PSA unit as disclosed herein can provide a low cost alternative to traditional revamps. An OCM unit with a PSA unit retrofitted to an existing steam cracker can be an effective way of adding ethylene capacity at a low marginal cost. The advantages of adding a PSA unit include that no additional cryogenic separation is required for the added capacity. For ethylene revamps, one of the key areas during debottlenecking may be the refrigeration systems and/or the fractionation columns, but utilizing the PSA to separate or pre-separate the additional product stream can result in a simpler and easier debottlenecking. As in shown in FIG. 13, for example, the tail gas from the PSA can be sent to the cracker system where the ethylene is recovered.

FIG. 13 shows an example of an OCM process integrated with an existing ethylene cracker using a PSA system for separations. The OCM reactor 1301 takes in methane 1310 and oxygen 1311 and produces an OCM effluent 1312 having $CO_2$, $CH_4$ and $C_2H4$, in some cases amongst other components, such as $H_2$ and CO. The OCM reaction can be exothermic and can produce steam 1313. The OCM effluent can be compressed in a compressor 1302 and optionally treated in an acid gas removal system 1303, and fed into a pressure swing adsorption (PSA) unit 1304. In some cases the acid gas removal system may have an additional knock out drum to condense and separate any condensates and water. It also can include a drier to remove water. The PSA unit can produce a product stream that can include $H_2$, $CH_4$, ethane, $CO_2$ and CO. The overhead stream 1315 can be fed into a methanation subsystem 1305 (e.g., methanation reactor) to provide methane for the OCM reactor, and some of the overhead stream can be purged 1316 to a fuel gas system, for example. Additional methane can be provided by way of a natural gas stream or other methane stream. The PSA tail gas 1317 can comprise most of the ethylene, the content of which may range from 50% to 99.9% depending on the process configuration and operation of the PSA system. The PSA tail gas can also comprise $H_2$, CO, $CO_2$, $CH_4$, ethane, propane, propylene, butanes, butenes, and other components. The process of FIG. 13 can further include an existing ethylene cracker 1306. The PSA tail gas can be fractionated using existing separations capacity in the ethylene cracker. The heavy components can be processed in the fractionation towers of the ethylene cracker, optionally first being compressed in the existing process gas compressor of the ethylene cracker. In some cases, the heavy components stream can be routed to the $CO_2$ removal unit of the existing ethylene cracker subsystem to meet the $CO_2$ specification. The OCM reactor can receive a $C_2$ recycle stream 1319 from the cracker complex.

The combination of a new OCM unit and an existing ethylene cracker can provide synergistic benefits. It can provide for a low cost alternative to add ethylene capacity to the existing cracker. In some cases, prior to retrofit of an ethylene cracker with OCM, the entire overhead from the existing demethanizer is used as fuel gas, and can now be available as one of the feeds to the methanation unit. In some cases, the demethanizer overhead off-gas comprises up to 95% methane, which can be converted to ethylene in the OCM reactor, hence increasing the total ethylene capacity. In some cases, the hydrogen content in the existing demethanizer overhead is substantial, and may be enough to meet the hydrogen requirement of the methanation unit.

In some cases, retrofitting an ethylene cracker with OCM reduces (or allows for reduction of) the severity of cracking in the existing cracker, enabling value addition by increasing the production of pyrolysis gasoline components in the cracker effluent, as the OCM reactor produces the ethylene that may be needed to achieve the total system capacity. The cracker can then be operated on high propylene mode to produce more propylene and at the same time meeting the ethylene production rate by the new OCM unit. This retrofit can result in greater flexibility for the ethylene producer with respect to the existing cracker operation.

In some instances, the overall carbon efficiency can be increased as the methane and hydrogen from the existing demethanizer off-gases can be utilized to convert the carbon dioxide and carbon monoxide to methane, which is fed to the OCM reactor.

In some instances, ethane and/or propane recycle streams from the existing cracker can be routed to the OCM unit (e.g., instead of the cracking furnaces). These recycle streams are typically routed to the cracking furnaces where they are cracked to extinction. This can provide an advantage over routing the recycle streams to OCM over the cracking furnace, such as higher selectivity to ethylene in the OCM process.

Figure 14:
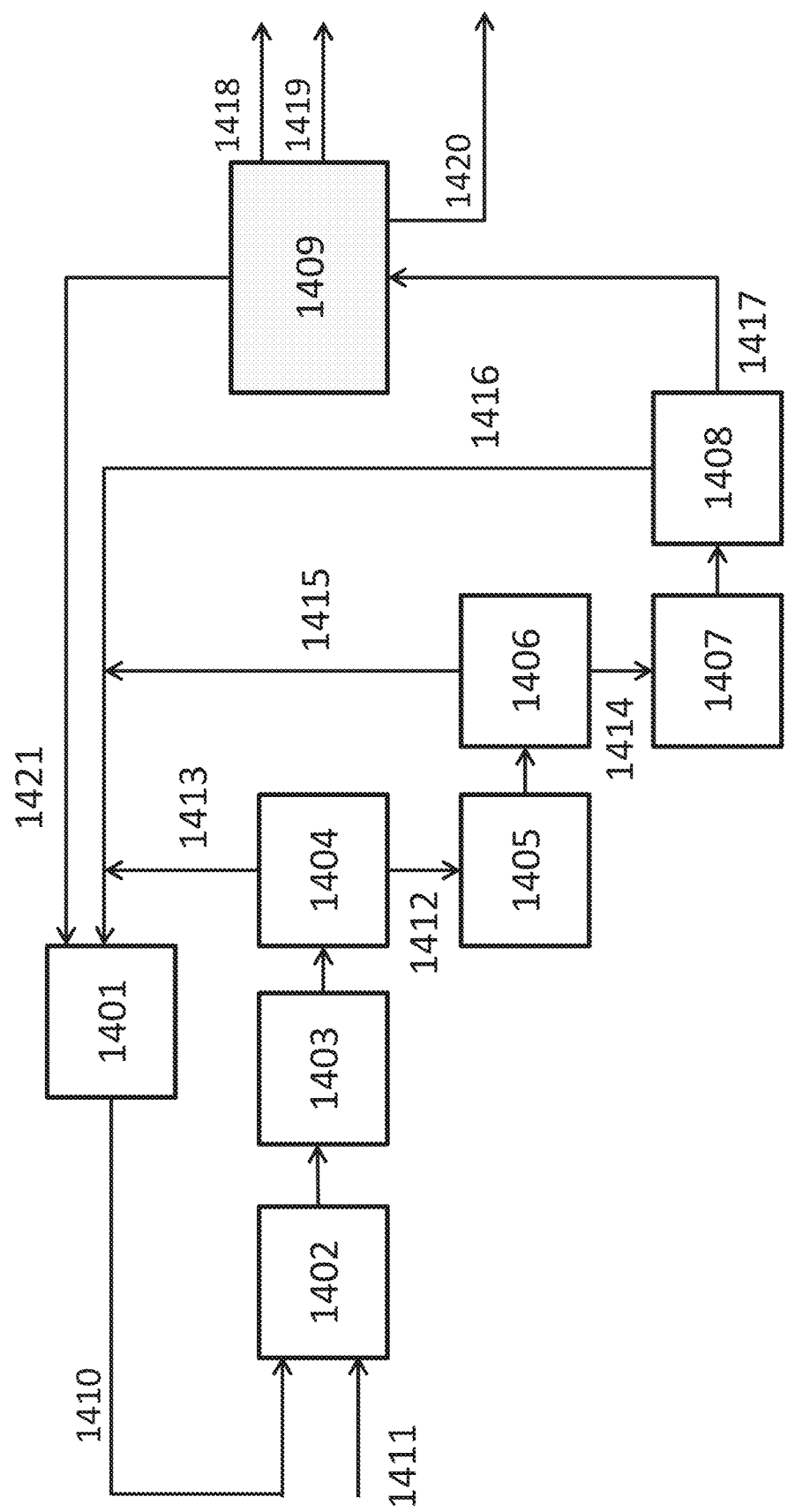
FIG. 14 shows an exemplary retrofit of OCM to a cracker, with a multi stage PSA unit.

In certain cases, more than one stages or PSA columns may be employed to achieve higher recovery and higher product purity. As in shown FIG. 14, for example, up to 99.9% recovery is possible using the multi stage PSA units. An OCM reactor 1402 can receive a methane stream 1410 and an oxygen stream 1411, and react the methane and oxygen to produce higher hydrocarbon products including ethylene in an OCM product stream. The OCM product stream can be compressed in a first compressor 1403 and directed to a first PSA separation 1404. The tail gas 1412 from the first PSA can be compressed in a second compressor 1405 and fed to a second PSA separation 1406, the tail gas 1414 from which can be compressed in a third compressor 1407 and separated in a third PSA separation 1408. The tail gas from the third PSA can be the final purified stream 1417 can be directed to a cracker unit, such as an existing cracker unit, where it can be processed and separated into an ethylene product stream 1418, a propylene product stream 1419, and an additional product stream 1420. PSA product streams 1413, 1415, and 1416 can be directed to recycle, such as via a methanation unit 1401, along with a demethanizer off gas stream 1421 from the cracker unit. Each PSA stage can be a dual-bed PSA or a multi-bed PSA system.

The application of a PSA unit to OCM systems, stand-alone or retrofits to existing facilities exhibits immense potential in terms of cost savings and ease of integration and retrofit to existing facilities.

ETL Systems

Figure 15:
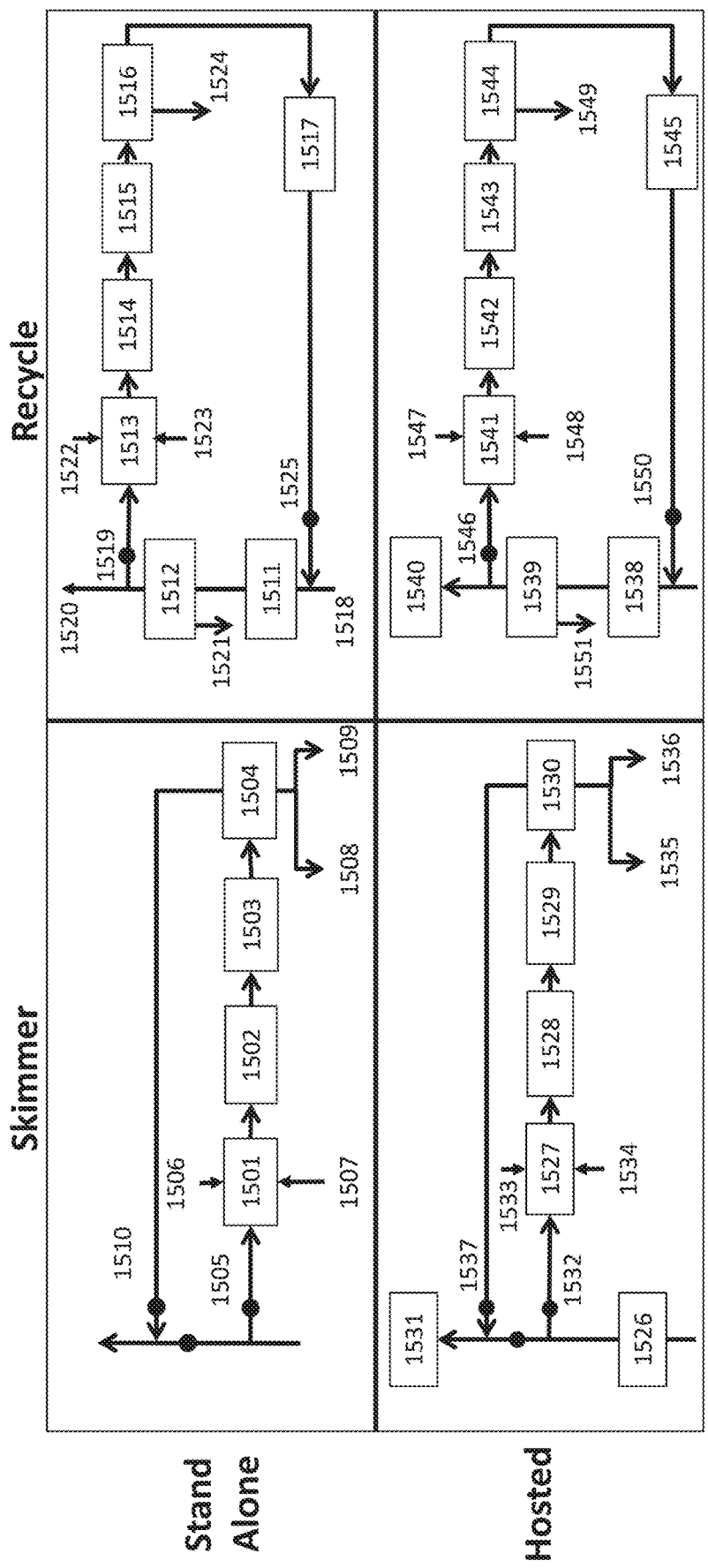
FIG. 15 shows exemplary configurations of ethylene to liquids (ETL) systems without PSA.

FIG. 15 shows various exemplary configurations for an OCM-ETL process. In the upper left, FIG. 15 shows a stand alone skimmer configuration, where a methane stream 1505 can be directed into an OCM reactor 1501 with an oxygen feed 1506 and optionally an ethane feed 1507. The OCM reactor product stream can be directed into a compressor 1502 and then into an ETL reactor 1503. The ETL product stream can be directed into a gas separations unit 1504, where it can be separated into a $C_{2+}$ product stream 1508, a $C_{5+}$ product stream 1509, and an overhead stream 1510 comprising methane which can be returned to a pipeline, sold to a consumer, or otherwise used. In the upper right, FIG. 15 shows a stand alone recycle configuration, where a methane feed stream 1518 (e.g., from a natural gas pipeline) is directed into a treatment unit 1511 and then into a separations system (e.g., cryogenic) 1512. A methane feed stream 1519 can be directed to an OCM reactor 1513, while another methane stream 1520 can be purged or used for power generation. A $C_{2+}$ stream 1521 can also be recovered from the separations system. An oxygen feed stream 1522 and optionally an ethane stream 1523 can also be directed into the OCM reactor, and the reactor can produce an OCM product stream. The OCM product stream can be directed into a compressor 1514 and then into an ETL reactor 1515. The ETL product stream can be processed in a knockout drum 1516 or other separator to remove a $C_{5+}$ product stream 1524. The remaining ETL product stream can be directed to a compressor 1517 and recycled to the treatment unit. In the lower left, FIG. 15 shows a hosted skimmer configuration, where a methane stream 1532 can be directed from a separations system 1526 (e.g., cryogenic) into an OCM reactor 1527 with an oxygen feed 1533 and optionally an ethane feed 1534. The OCM reactor product stream can be directed into a compressor 1528 and then into an ETL reactor 1529. The ETL product stream can be directed into a gas separations unit 1530, where it can be separated into a $C_{2+}$ product stream 1535, a $C_{5+}$ product stream 1536, and an overhead stream 1537 comprising methane which can be returned to a recompressor 1531. In the lower right, FIG. 15 shows a hosted recycle configuration, where a methane stream is directed into a treatment unit 1538 and then into a separations system (e.g., cryogenic) 1539. A methane feed stream 1546 can be directed to an OCM reactor 1541, while another methane stream can be directed to a recompressor 1540. A $C_{2+}$ stream 1551 can also be recovered from the separations system. An oxygen feed stream 1547 and optionally an ethane stream 1548 can also be directed into the OCM reactor, and the reactor can produce an OCM product stream. The OCM product stream can be directed into a compressor 1542 and then into an ETL reactor 1543. The ETL product stream can be processed in a knockout drum 1544 or other separator to remove a $C_{5+}$ product stream 1549. The remaining ETL product stream can be directed to a compressor 1545 and recycled 1550 to the treatment unit.

Figure 16:
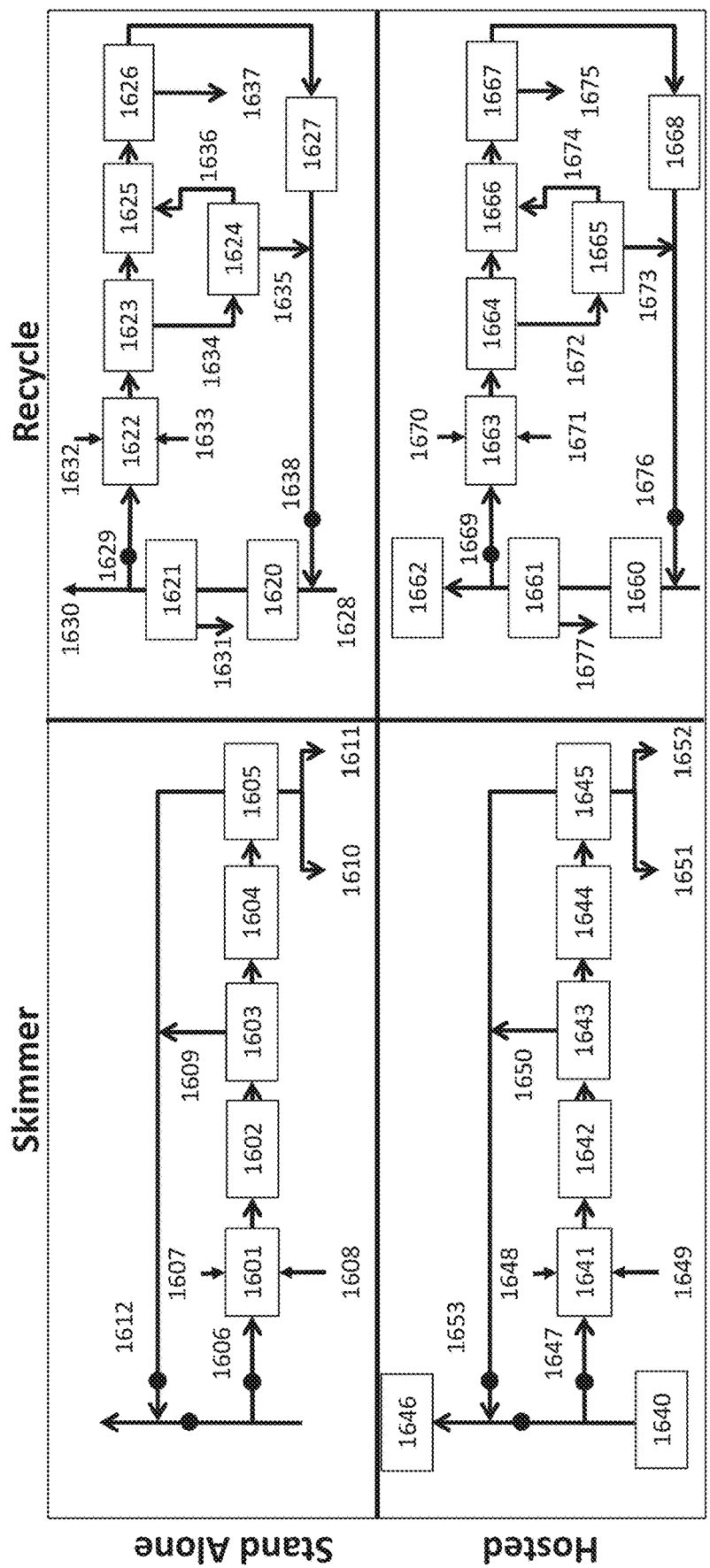
FIG. 16 shows exemplary configurations of ETL systems with PSA.

FIG. 16 shows similar configurations as FIG. 15, with an added pressure swing adsoprtion (PSA) unit to pre-separate the OCM effluent to remove most of the methane, hydrogen, CO and $CO_2$ from the olefinic stream, which is then fed to the ETL reactor. This can result in a feed to the ETL reactor that is concentrated in olefins. Though the process remains similar, the entire ETL and separations train becomes considerably smaller; that is, larger capacities can be achieved in the same set-up or same footprint. In some cases this can improve the ETL reaction operation. In the upper left, FIG. 16 shows a stand alone skimmer configuration, where a methane stream 1606 can be directed into an OCM reactor 1601 with an oxygen feed 1607 and optionally an ethane feed 1608. The OCM reactor product stream can be directed into a compressor 1602 and then into a PSA unit 1603. A light stream 1609 comprising methane, hydrogen, CO and $CO_2$ can be directed from the PSA back to a pipeline, sold to a consumer, or otherwise used. An olefinic stream can be directed from the PSA to an ETL reactor 1604. The ETL product stream can be directed into a gas separations unit 1605, where it can be separated into a $C_{2+}$ product stream 1610, a $C_{5+}$ product stream 1611, and an overhead stream 1612 comprising methane which can be returned to a pipeline, sold to a consumer, or otherwise used. In the upper right, FIG. 16 shows a stand alone recycle configuration, where a methane feed stream 1628 (e.g., from a natural gas pipeline) is directed into a treatment unit 1620 and then into a separations system (e.g., cryogenic) 1621. A methane feed stream 1629 can be directed to an OCM reactor 1622, while another methane stream 1630 can be purged or used for power generation. A $C_{2+}$ stream 1631 can also be recovered from the separations system. An oxygen feed stream 1632 and optionally an ethane stream 1633 can also be directed into the OCM reactor, and the reactor can produce an OCM product stream. The OCM product stream can be directed into a compressor 1623, and at least a portion 1634 of the OCM product stream can be directed from the compressor into a PSA unit 1624. A light stream 1635 comprising methane, hydrogen, CO and $CO_2$ can be directed from the PSA back to the treatment unit. An olefinic stream 1636 can be directed from the PSA to an ETL reactor 1625. The ETL product stream can be processed in a knockout drum 1626 or other separator to remove a $C_{5+}$ product stream 1637. The remaining ETL product stream can be directed to a compressor 1627 and recycled to the treatment unit. In the lower left, FIG. 16 shows a hosted skimmer configuration, where a methane stream 1647 can be directed from a separations system 1640 (e.g., cryogenic) into an OCM reactor 1641 with an oxygen feed 1648 and optionally an ethane feed 1649. The OCM reactor product stream can be directed into a compressor 1642 and then into and then into a PSA unit 1643. A light stream 1650 comprising methane, hydrogen, CO and $CO_2$ can be directed from the PSA to a recompressor 1646. An olefinic stream can be directed from the PSA to an ETL reactor 1644. The ETL product stream can be directed into a gas separations unit 1645, where it can be separated into a $C_{2+}$ product stream 1651, a $C_{5+}$ product stream 1652, and an overhead stream 1653 comprising methane which can be returned to the recompressor. In the lower right, FIG. 16 shows a hosted recycle configuration, where a methane stream is directed into a treatment unit 1660 and then into a separations system (e.g., cryogenic) 1661. A methane feed stream 1669 can be directed to an OCM reactor 1663, while another methane stream can be directed to a recompressor 1662. A $C_{2+}$ stream 1677 can also be recovered from the separations system. An oxygen feed stream 1670 and optionally an ethane stream 1671 can also be directed into the OCM reactor, and the reactor can produce an OCM product stream. The OCM product stream can be directed into a compressor 1664 and at least a portion 1672 of the OCM product stream can be directed from the compressor into a PSA unit 1665. A light stream 1673 comprising methane, hydrogen, CO and $CO_2$ can be directed from the PSA back to the treatment unit. An olefinic stream 1674 can be directed from the PSA to an ETL reactor 1666. The ETL product stream can be processed in a knockout drum 1667 or other separator to remove a $C_{5+}$ product stream 1675. The remaining ETL product stream can be directed to a compressor 1668 and recycled 1676 to the treatment unit.

The ETL reactor can be a tubular, packed bed, moving bed, fluidized bed, or other reactor type. An ETL reactor can be an isothermal or adiabatic reactor. The ETL system can benefit from a feed concentrated in olefins. The ETL reactor system can use a recycle stream to control and moderate the temperature increase in the reactor bed due to the highly exothermic nature of the ETL reactions. ETL systems are described in, for example, U.S. patent application Ser. No. 14/591,850, which is entirely incorporated herein by reference.

In certain embodiments, one or more of the fractionation towers can be deemed redundant if using the PSA, as an example, a demethanizer may not be required and the sales gas or purge gas to fuel can be sent from the PSA itself.

Retrofit Applications for Midstream and Refining

Figure 17:
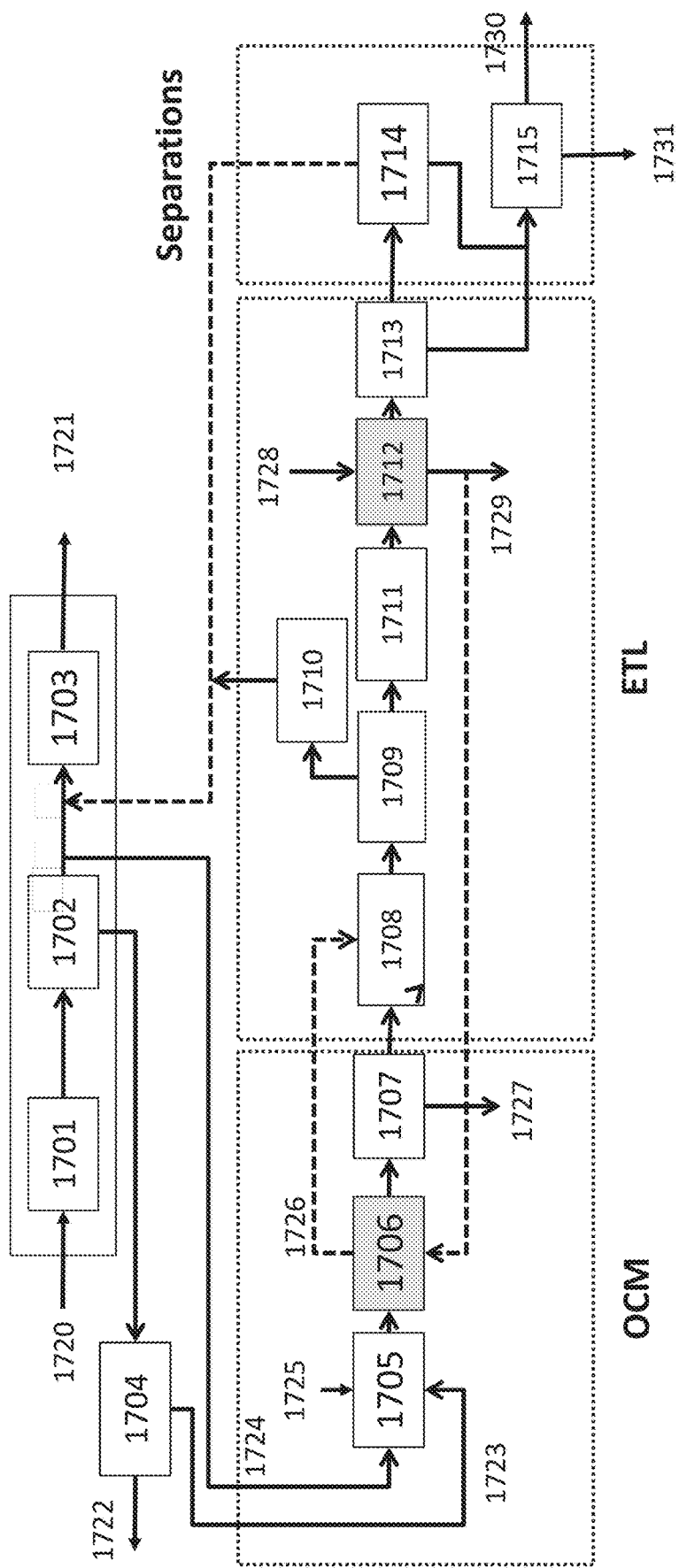
FIG. 17 shows an exemplary PSA unit integrated with an OCM-ETL system for a midstream application.

Systems, such as those of FIG. 17, can be integrated with an existing gas processing plant where one or more of the existing subsystems can be utilized. The utilization may arise from the fact that the existing subsystems are no longer used, or have an additional capacity available to allow for the integration.

FIG. 17 shows an exemplary application of an OCM-ETL system using a PSA system for pre-separations to an existing gas processing plant, where one or more existing sub systems may be utilized. As shown in FIG. 17, the existing separations sub-system can be integrated with the OCM-ETL system to add value by converting natural gas to higher value liquid hydrocarbons. The PSA unit can be used to pre-separate the lighter components like methane, hydrogen, carbon monoxide, carbon dioxide, ethane, and other components, and the olefin rich stream can be sent to the ETL reactor that converts the olefins to higher molecular weight liquid hydrocarbons. One advantage of using a PSA system is the reduction in net additional feed to the existing separation system, which can be de-bottlenecked easily. If the separation system is no longer in use, addition of a PSA can bring about larger total capacities that can be achieved by adding larger OCM-ETL systems. A natural gas stream 1720 can be directed to a treatment unit 1701 and then into a separations system (e.g., cryogenic) 1702. At least portion of a methane stream 1724 from the separations unit can be directed to an OCM reactor 1705, while a portion of the methane stream can be directed to a compressor 1703 and used as sales gas 1721 or other purposes. A higher hydrocarbon stream can be directed from the separations system to a $C_2$ removal unit 1704, which can produce a natural gas liquids stream 1722 and a $C_2$ stream 1723. The $C_2$ stream can be fed into the OCM reactor with the methane stream and an oxygen stream 1725, and reacted to form higher hydrocarbon products including ethylene. The OCM product stream can be directed into a heat recovery system 1706, which can generate a high pressure superheated (HPSH) steam stream 1726. The OCM product stream can then be directed to a knockout drum to recover a condensate stream 1727. The OCM product stream can then be directed to a compressor 1708, which can operate using the HPSH steam stream. From the compressor, the OCM product stream can be directed to a PSA unit 1709. From the PSA unit, light stream comprising methane, hydrogen, CO and $CO_2$ can be directed to a methanation unit 1710, and an olefinic stream can be directed to an ETL reactor 1711 and reacted to form higher hydrocarbon products. The ETL product stream can be directed to a heat recovery unit 1712, where boiler feed water (BFW) 1728 can be heated, at least a portion of which can be fed 1729 to the heat recovery unit 1706. The ETL product stream can then be directed to another knockout drum 1713. The overhead stream from the knockout drum can be directed to a low temperature separations unit 1714, while the bottoms stream from the knockout drum can be directed to a $C_4$ removal unit 1715, which can produce a $C_4$ stream 1730 and a $C_{5+}$ stream 1731. Overhead from the low temperature separations unit, as well as product from the methanation reactor, can be directed back to the compressor 1703.

Figure 18:
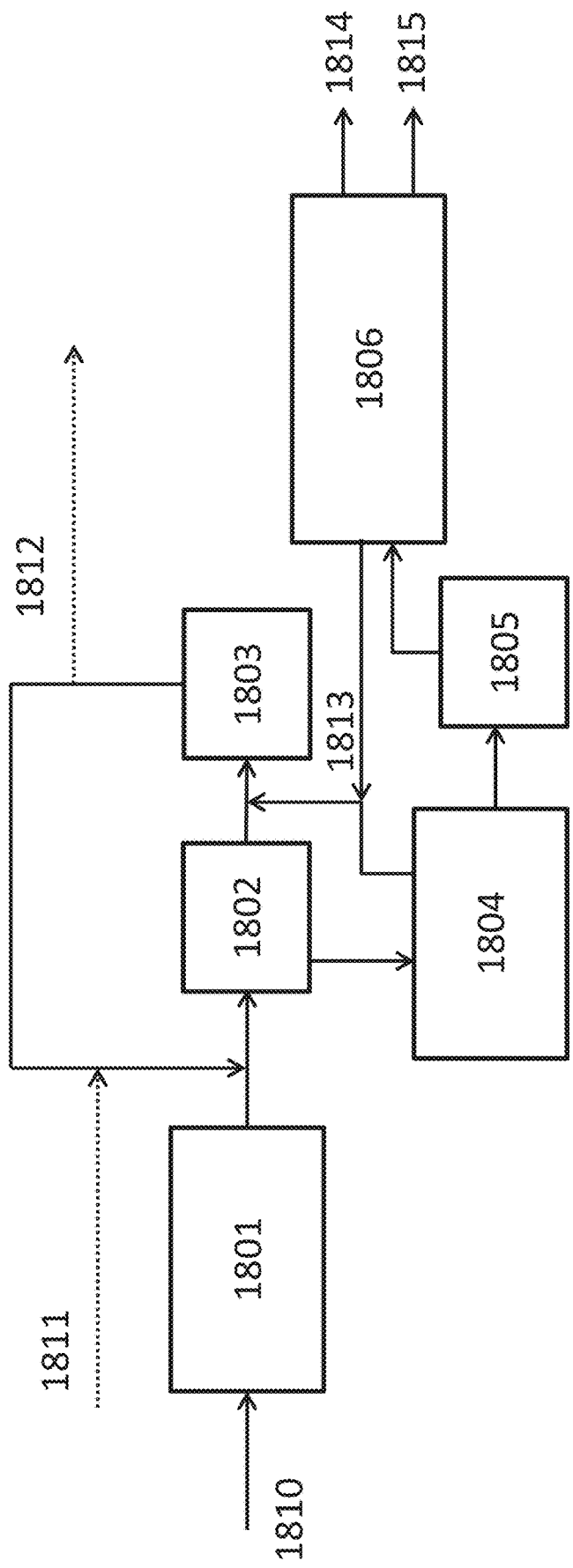
FIG. 18 shows an exemplary PSA unit integrated with an OCM-ETL system in a natural gas liquids (NGL) application.

OCM-ETL systems of the present disclosure can be integrated into and combined into conventional NGL extraction and NGL fractionation sections of a midstream gas plant. Where NGLs in the gas stream are declining (or gas is dry), the deployment of OCM-ETL can utilize an existing facility to produce additional liquid streams. The implementation of OCM-ETL can allow for the generation of on specification "pipeline gas." The products from the facility can be suitable for use (or on specification or "spec") as pipeline gas, gasoline product, hydrocarbon (HC) streams with high aromatic content, and mixed $C_4$ products. The PSA systems discussed above can be employed to separate, pre-separate or purify the hydrocarbon feed streams in the integrated NGL OCM-ETL system. FIG. 18 shows an exemplary NGL extraction facility integrated with an OCM-ETL system. As shown in FIG. 18, for example, the feed to the PSA 1802 can be the net incoming gas from the treatment system 1801, which can treat a methane stream (e.g., natural gas) 1810. The PSA system can separate the feed to the OCM reactor 1803, which is mostly methane and lighter components with some ethane to utilize a PBC section of the OCM reactor, and the feed to the ETL reactor 1805, which can first be processed in a natural gas liquids extraction system 1804. The feed to the ETL system can be the PSA tail gas and OCM effluent comprising ethylene, propylene, ethane, propane, hydrogen, methane, and other components. In some cases, the OCM effluent can be directly fed to the ETL reactor. In some cases the OCM effluent is hydrogenated and fed to the ETL system. In some cases, as shown for example in FIG. 18, the OCM effluent is fed back to the PSA unit for separation; additional natural gas 1811 can be added, and a stream can be recovered 1812 (e.g., for use as pipeline gas). In some examples, the system may have a methanation unit that takes in the effluent from ETL reactor or OCM reactor and converts the CO, $CO_2$ and $H_2$ to methane, thereby further increasing the carbon efficiency of the process. The existing NGL extraction and product fractionation 1806 sub-systems can then be used to fractionate the final products, including into a mixed $C_4$ stream 1814 and a $C_{5+}$ product stream 1815.

Refining

Refinery gas typically contains valuable components like hydrogen, methane, ethane, ethylene, propane, propylene, and butane. Most commonly, refinery off-gases (ROG) are exported to the fuel gas system, thereby losing the value of the components contained therein. The OCM-ETL process can be used to improve the value of products as the OCM converts the methane to ethylene and the ETL converts olefins (e.g., those existing in the ROG and those generated by OCM) to higher value liquids as $C_4$ components, gasoline blends, or aromatic components.

Figure 19:
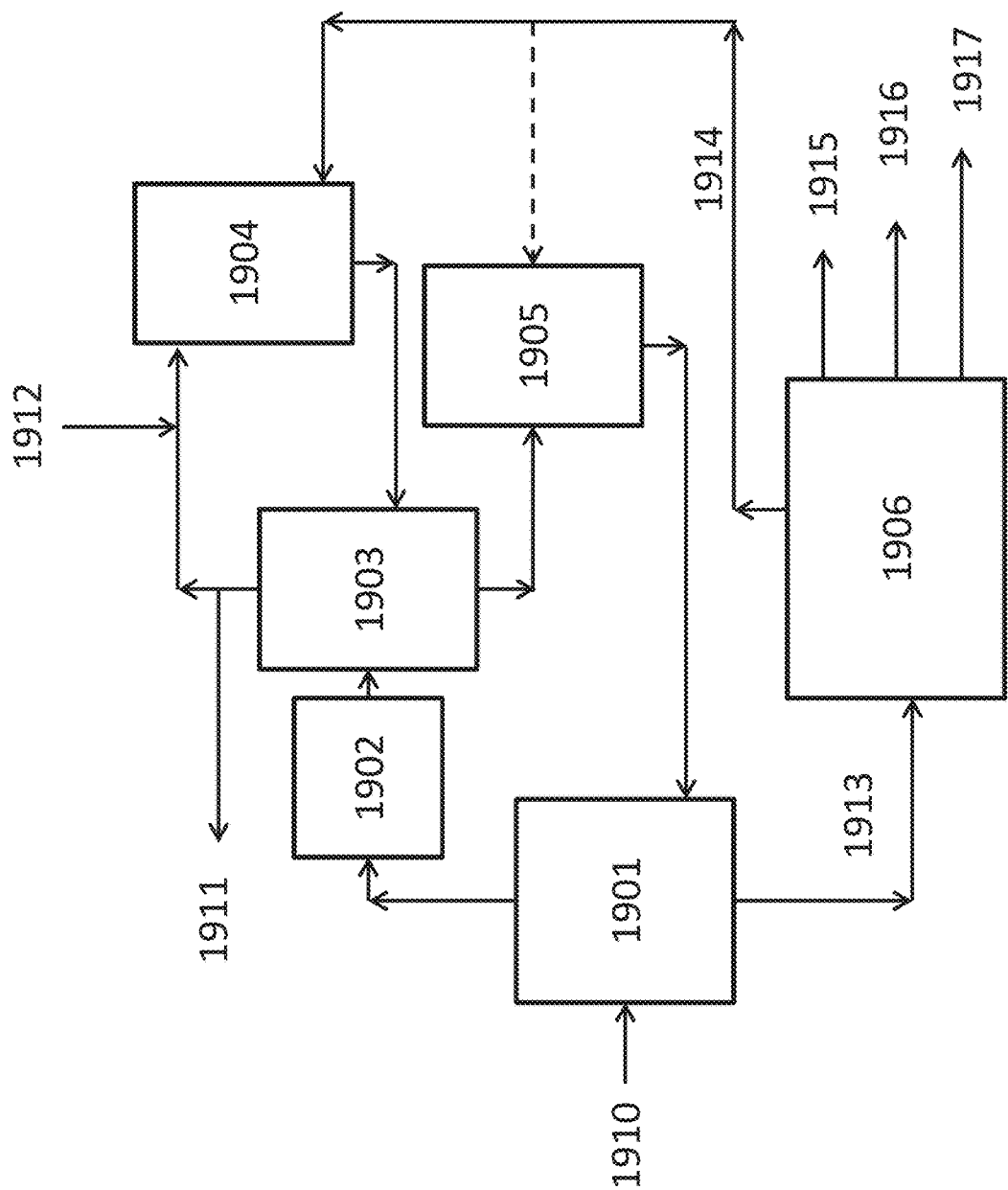
FIG. 19 shows an exemplary PSA unit integrated with an OCM-ETL system for a refining application.

FIG. 19 shows an exemplary PSA unit integrated to a refinery process scheme. A refinery gas plant 1901 can receive gas 1910 from cracking or other units. The PSA unit 1903 (after, for example, treatment of the gas in a treatment unit 1902) can separate components in refinery gas plant off gas to methane and a $C_{2+}$ cut which contains most or all of the olefinic materials. The methane can be used as refinery fuel 1911 and/or directed to an OCM unit 1904 with post-bed cracking. The OCM feed can be supplemented with additional natural gas 1912. The olefinic materials can be directed to an ETL reactor 1905. The OCM effluent can also be routed to the PSA where the olefins produced in the OCM are also sent to the ETL reactor. In some cases, the OCM effluent can be routed to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component from 1 to 99%. A $C_{3+}$ stream 1913 from the refinery gas plant can be directed to a product fractionation system 1906, which can provide a $C_2/C_3$ stream 1914 (which can be directed to the OCM reactor), an $iC_4$ stream 1915, a gasoline blend stream 1916, and/or a kerosene/jet stream 1917.

Figure 20:
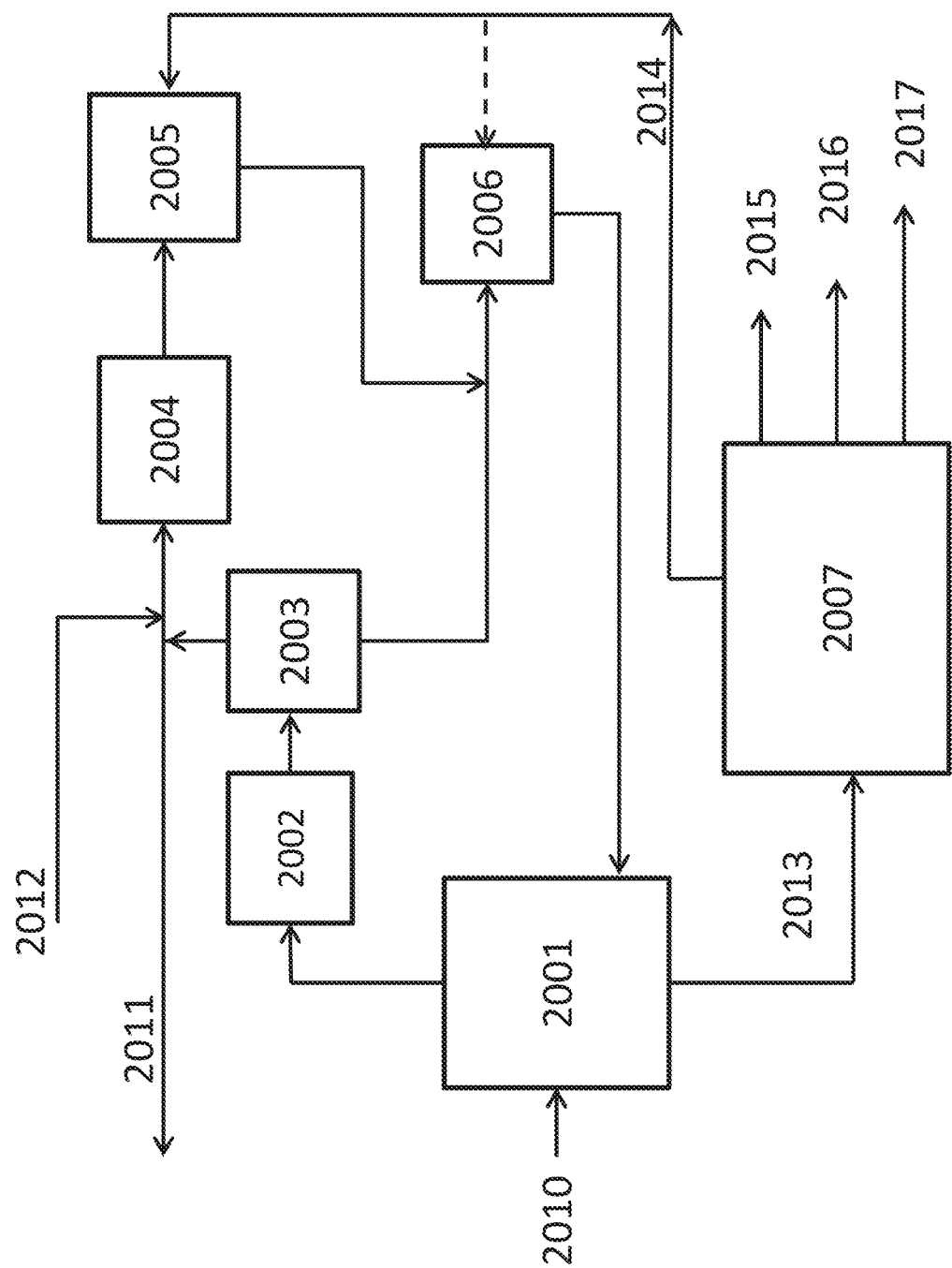
FIG. 20 shows an exemplary alternate scheme for a PSA unit integrated with an OCM-ETL system for a refining application.

As shown in FIG. 20, in some cases the system can have a methanation unit to further improve the carbon efficiency of the process. A refinery gas plant 2001 can receive gas 2010 from cracking or other units. The PSA unit 2003 (after, for example, treatment of the gas in a treatment unit 2002) can separate components in refinery gas plant off gas to methane and a $C_{2+}$ cut which contains most or all of the olefinic materials. The methane can be used as refinery fuel 2011 and/or directed to a methanation unit 2004, and then to an OCM reactor 2005 with post-bed cracking. The methanation feed can be supplemented with additional natural gas 2012. The olefinic materials can be directed to an ETL reactor 2006. The OCM effluent can be routed to the ETL reactor. In some cases, the OCM effluent can also be routed to the PSA where the olefins produced in the OCM are also sent to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component from 1 to 99%. A $C_{3+}$ stream 2013 from the refinery gas plant can be directed to a product fractionation system 2007, which can provide a $C_2/C_3$ stream 2014 (which can be directed to the OCM reactor), an $iC_4$ stream 2015, a gasoline blend stream 2016, and/or a kerosene/jet stream 2017.

Methods and systems of the present disclosure can be combined with or modified by other methods and systems, such as those described in U.S. patent application Ser. No. 14/591,850, filed Jan. 7, 2015, now published as U.S. Patent Pub. No 2015/0232395; U.S. patent application Ser. No. 13/936,783, filed Jul. 8, 2013, now published as U.S. Patent Pub. No. 2014/0012053; U.S. patent application Ser. No. 13/936,870, filed Jul. 8, 2013, now published as U.S. Patent Pub. No. 2014/0018589; U.S. patent application Ser. No. 13/900,898, filed May 23, 2013, now published as U.S. Patent Pub. No 2014/0107385; U.S. patent application Ser.

No. 14/553,795, filed Nov. 25, 2014, now published as U.S. Patent Pub. No. 2015/0152025; U.S. patent application Ser. No. 14/592,668, filed Jan. 8, 2015, now published as U.S. Patent Pub. No. 2015/0210610; and U.S. patent application Ser. No. 14/789,953, filed Jul. 1, 2015, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating compounds with two or more carbon atoms ($C_{2+}$ compounds), comprising:
   (a) directing oxygen ($O_2$) and methane ($CH_4$) into an oxidative coupling of methane (OCM) reactor that reacts said $O_2$ and $CH_4$ in an OCM process to yield a product stream comprising (i) $C_{2+}$ compounds including ethylene ($C_2H_4$) and (ii) carbon monoxide (CO) and/or carbon dioxide ($CO_2$); and
   (b) directing said product stream from said OCM reactor into a separations system that employs a refrigeration unit having a refrigerant that includes methane from said product stream, to enrich said $C_{2+}$ compounds in said product stream.

2. The method of claim 1, wherein said product stream is directed into said separations system through one or more additional units.

3. The method of claim 1, further comprising separating methane from said product stream for use in said refrigeration unit.

4. The method of claim 1, further comprising directing CO and/or $CO_2$ from said product stream to a methanation reactor that reacts said CO and/or $CO_2$ to yield a methanation product stream comprising methane.

5. The method of claim 4, further comprising directing at least a portion of said methane in said methanation product stream to said OCM reactor.

6. The method of claim 1, further comprising separating said product stream into (i) an ethylene product stream comprising ethylene and (ii) a $C_{3+}$ product stream comprising compounds with three or more carbon atoms ($C_{3+}$ compounds).

7. The method of claim 1, further comprising directing ethane from said product stream to said OCM reactor.

8. The method of claim 1, further comprising, prior to directing said product stream into said separations system, compressing said product stream.

* * * * *